US006872839B1

(12) United States Patent
Feiler et al.

(10) Patent No.: US 6,872,839 B1
(45) Date of Patent: Mar. 29, 2005

(54) BENZOFURAN-2-ONE

(75) Inventors: Leonhard Feiler, Neuenburg (DE); Thomas Ruch, Basel (CH); Olof Wallquist, Therwil (CH); Peter Nesvadba, Marly (CH)

(73) Assignee: Cibaspecialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 09/518,464

(22) Filed: Mar. 3, 2000

(30) Foreign Application Priority Data

Mar. 10, 1999 (CH) ............................................. 447/99

(51) Int. Cl.$^7$ ................... C07D 307/78; C07D 307/87; C07D 307/93
(52) U.S. Cl. ...................... 549/302; 549/303; 549/304; 549/307; 549/308; 549/309; 549/310; 548/454; 548/472
(58) Field of Search ................ 549/302, 303, 549/304, 307, 308, 309, 310; 548/454, 472

(56) References Cited

U.S. PATENT DOCUMENTS

| 2,701,257 A | | 2/1955 | Thomas ...................... 260/461 |
| 3,033,875 A | * | 5/1962 | Nutting et al. ............... 548/454 |
| 4,400,507 A | | 8/1983 | von der Crone ............ 544/300 |
| 5,614,572 A | | 3/1997 | Nesvadba et al. ........... 524/111 |
| 5,626,633 A | | 5/1997 | Roschger ....................... 8/506 |
| 5,747,566 A | | 5/1998 | Weber .......................... 524/93 |

FOREIGN PATENT DOCUMENTS

| DE | 1 959 262 | 3/1970 |
| DE | 21 42 245 | 9/1980 |
| DE | 28 14 526 | 1/1988 |
| EP | 0 632 102 | 1/1995 |
| EP | 788 890 | 8/1997 |
| EP | 921 435 | 6/1999 |
| WO | 80/01566 | 8/1980 |
| WO | 99 13007 | 3/1999 |
| WO | 00 24736 | 5/2000 |

OTHER PUBLICATIONS

Chemical Abstracts 51:43285, Rearrangements of hydroxy-diquinones. II.Posternak, Th.; Huguenin, R.; Alcalay, W. (Univ. Lausanne, Switz.). Helv. Chim. Acya, 39, 1564–79 (French) 1956.*
Becker et al. J. Org. Chem. vol. 42, No. 18, (1977) pp. 2966–2973.
Jerry March, Advanced Organic Chemistry, Ed. (1977), pp. 824, 817 & 810.
Z. Ma et al, J. Org. Chem. vol. 56, (1991), pp. 6110–6114.
W.A.P. Reyen, Synthesis, pp. 624 & 625 (1976).
O.S. Wolfbeis et al., in Z. Naturforsch. 34b, pp. 283–289.
P. Nesvadba et al., Synlett (1999)pp. 863 & 864.
Burke et al. Tetrahedron, vol. 53, No. 25, Jun. 23, 1997, pp. 8491–8500.
Nicolaides et al., J. Che. Soc. Perkin Trans. 1 (1992) (2) pp. 283–289.
Y. Takeuchi et al., Chem. Pharm. Bull. (1990), 38 (8), pp. 2265–2267.
Gadre et al. Synth, Commun. (1988), 18(9). Pp. 1015–27.
Soliman et al.Phosphorus Sulfur (1988), 35 (102), pp. 41–46.
Sunitha et al. Tetrahedron (1987), 43, (14) pp. 3269–3278.
Chatterjea et al. J. Chem. Res. Synop. (1979) (11) pp. 356.
Friedrichsen, Justus Liebigs Ann. Chem. (1975) (9) pp. 1545–1562.
Chan, et al. Aust. J. Chem. (1975) 28(5) PP. 1097–111.
Geier et al., Acta Chem. Scand. Ser. B. (1974), 28(7) pp. 717–719.
Chan et al. Syn. Commun. (1972), 2(6) pp. 409–414.

* cited by examiner

Primary Examiner—Kriellion A. Sanders
(74) Attorney, Agent, or Firm—Tyler A. Stevenson; David R. Crichton

(57) ABSTRACT

Benzofuran-2-ones, compositions comprising benzofuranones, processes for preparing them, and their use as colorants for high or low molecular mass organic material.

2 Claims, No Drawings

BENZOFURAN-2-ONE

The invention relates to novel benzofuran-2-ones, to processes for preparing them and to their use as colorants for organic materials, especially organic materials of high molecular mass or low molecular mass.

Benzofuran-2-one polymer stabilizers are known, for example, from WO 80/01566. From EP 632 102-B1 it is known that benzofuran-2-ones may be used for the mass colouring of plastics. These products, however, go only part-way towards meeting the present-day requirements in terms of applicational properties.

The object of the present invention is therefore to provide novel benzofuran-2-ones which in addition to good performance properties such as heat stability and light fastness give rise to strong, transparent and bright colourations. The object was, moreover, to provide processes for preparing novel benzofuran-2-ones that meet the present-day needs for an ecological process.

The present invention accordingly provides compounds of the formulae (Ia), (Ib) or (Ic)

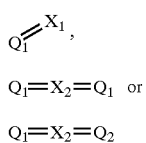
(Ia)

$Q_1=X_2=Q_1$ or (Ib)

$Q_1=X_2=Q_2$ (Ic)

in which
$Q_1$ is a benzofuran-2-one of formula (IIa), and
$Q_2$ is a benzofuran-2-one of the formula (IIb)

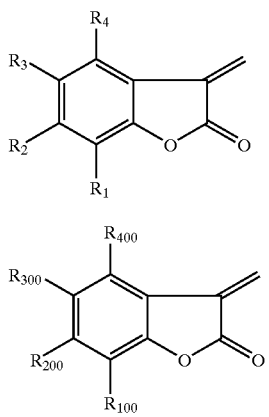

in which
$R_1$, $R_2$, $R_3$, $R_4$, $R_{100}$, $R_{200}$, $R_{300}$ or $R_{400}$ independently of one another are hydrogen, halogen, cyano, ether, nitro, amine, amide, imine, urethane, ester, acid radical and also its salt form, $C_1$–$C_{24}$alkyl, $C_1$–$C_{24}$alkoxy, $C_1$–$C_{24}$alkylthio, $C_5$–$C_{12}$cycloalkyl, $C_5$–$C_{12}$cycloalkoxy, $C_5$–$C_{12}$cycloalkylthio, $C_2$–$C_{24}$alkenyl, $C_6$–$C_{24}$aryl, $C_6$–$C_{25}$aralkyl, $C_6$–$C_{24}$aryloxy, -thio or $A_5$–$A_{18}$heteroaryl, $A_5$–$A_{18}$heteroaryloxy, -thio, or
$R_1$ and $R_2$, $R_2$ and $R_3$, $R_3$ and $R_4$ or $R_{100}$ and $R_{200}$, or $R_{200}$ and $R_{300}$, $R_{300}$ and $R_{400}$ independently of one another but in each case in unison are divalent radicals, such as 1,3-butadien-1,4-ylene or —CH═CH—NH—, which produce a fused-on additional 5- or 6-membered ring, and
$X_1$ is a hydrazone or imine radical, with the proviso that, if $R_1$, $R_2$, $R_3$ or $R_4$ are hydrogen and/or methyl, the hydrazone radical is excluded, or, if $R_1$, $R_2$, $R_3$ or $R_4$ are hydrogen, the phenylimine and also 4-dimethylamine-phenylimine radical is excluded, or

is a methylene radical
in which
$Q_3$ and $Q_4$ independently of one another are $C_6$–$C_{24}$aryl, with the proviso that $Q_3$ and $Q_4$ are not phenyl, if $R_1$, $R_2$, $R_3$ or $R_4$ are hydrogen, or
independently of one another are hydrogen, or $C_6$–$C_{24}$aryl-substituted primary or secondary amine or $C_6$–$C_{24}$aryl, with the proviso that $R_3$ is not hydrogen, methoxy or hydroxyl, or
independently of one another are unsubstituted or substituted ($C_6$–$C_{24}$aryl)oxy and hydrogen, $C_1$–$C_{24}$alkyl, $C_1$–$C_{24}$alkoxy, $C_1$–$C_{24}$alkylthio radical, $C_5$–$C_{12}$cycloalkyl, $C_5$–$C_{12}$cycloalkoxy, $C_5$–$C_{12}$cycloalkylthio radical, $C_2$–$C_{24}$alkenyl, $C_6$–$C_{24}$aryl, $C_6$–$C_{24}$aryloxy, -thio or $A_5$–$A_{18}$heteroaryl, -thio, with the proviso that $Q_3$ and $Q_4$ are not methyl and —OCO-4-(1-chlorophenylene), or
$Q_3$ and $Q_4$ together are a lactam, barbituric acid or isoindoline radical, and

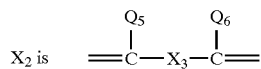

$X_2$ is in which
$X_3$ is a bridge to a further benzofuran-2-one (IIa) and/or (IIb), in which the bridge is a $A_5$–$A_{18}$heteroarylene, or 1,2- or 1,3-phenylene, substituted 1,4-phenylene, or polyether, polyimine, polyamine radical, or bi($C_6$–$C_{24}$)arylene or bi($A_5$–$A_{18}$)heteroarylene, which are connected to one another directly or via —C—, —N—, —O—, or a (—N═N—) unit, and
$Q_5$ and $Q_6$ independently of one another are $C_6$–$C_{24}$aryl, ($C_6$–$C_{24}$aryl)oxy and hydrogen, $C_1$–$C_{24}$alkyl, $C_1$–$C_{24}$alkoxy, $C_1$–$C_{24}$alkylthio radical, $C_5$–$C_{12}$cycloalkyl, $C_5$–$C_{12}$cycloalkoxy, $C_5$–$C_{12}$cycloalkylthio radical, $C_2$–$C_{24}$alkenyl, $C_6$–$C_{24}$aryl, $C_6$–$C_{24}$aryloxy, -thio or $A_5$–$A_{18}$heteroaryl, -thio,
or $X_2$ is

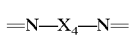

in which
$X_4$ is a bridge to a further benzofuran-2-one (IIa) and/or (IIb), in which the bridge is $C_6$–$C_{24}$arylene, $A_5$–$A_{18}$heteroarylene, or polymethylidene, polyether, polyimines, polyamines, or bi($C_5$–$C_{24}$)arylene or bi($A_6$–$A_{18}$)heteroarylene, which are connected to one another directly or via —C—, —N—, —O— or a (—N═N—) unit, or $X_2$ is

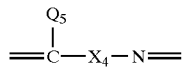

The invention also embraces tautomeric and polymorphic structures of the compounds of the formula (Ia), (Ib) or (Ic).

In one preferred embodiment of the invention, $R_1, R_2, R_3, R_4, R_{100}, R_{200}, R_{300}$ or $R_{400}$ independently of one another are hydrogen, halogen, cyano, $NO_2$, $NR_5R_6$, $NR_7COR_5$, $NR_7COOR_5$, $N=CR_5R_6$, $CONR_7R_8$, $OR_5$, $COOR_5$, $(C_1-C_{12}alkyl)$-$COOR_5$, $COO^-X^+$, $SR_5$, $SOR_5$, $SO_2R_5$, $SO_2NR_7R_8$, $SO_3R_5$ OR $SO_3^-X^+$, or are unsubstituted or mono- or poly-halogen-, -hydroxyl-, -oxo-, -cyano-, —$COOR_6$—, —$COO^-X^+$-substituted $C_1-C_{25}$alkyl, $C_5-C_{12}$cycloalkyl or $C_2-C_{24}$alkenyl, which may be uninterrupted or interrupted one or more times by O, S or $NR_6$, or are unsubstituted or mono- or poly-halogen-, -nitro-, -cyano-, —$OR_6$—, —$SR_6$—, $NR_7R_8$—, —$CONR_7R_8$—, —$COOR_6$—, —$COO^-X^+$—, —$SO_2R_6$, —$SO_2NR_7R_8$—, —$SO_3R_6$—, —$SO_3^-X^+$—, —$NR_7COR_8$— or —$NR_7COOR_6$-substituted $C_6-C_{18}$aryl, $C_7-C_{18}$aralkyl or $A_5-A_{18}$heteroaryl, or $R_1$ and $R_2$, $R_2$ and $R_3$, $R_3$ and $R_4$ or $R_{100}$ and $R_{200}$, or $R_{200}$ and $R_{300}$, $R_{300}$ and $R_{400}$ are for example divalent radicals, such as 1,3-butadien-1,4-ylene or —CH=CH—NH—, which produce a fused-on additional 5- or 6-membered ring, in which $R_5$ is unsubstituted or mono- or poly-halogen-, -hydroxyl-, -oxo-, -cyano-, —$COOR_6$—, —$COO^-X^+$-substituted $C_1-C_{25}$alkyl, $C_5-C_{12}$cycloalkyl or $C_2-C_{24}$alkenyl, which may be uninterrupted or interrupted one or more times by O, S or $NR_6$, or is unsubstituted or mono- or poly-halogen-, -nitro-, -cyano-, —$OR_6$—, —$SR_6$—, —$NR_7R_8$—, —$CONR_7R_8$—, —$COOR_6$—, —$COO^-X^+$—, —$SO_2R_6$—, —$SO_2NR_7R_8$—, —$SO_3R_6$—, $SO_3^-X^+$—, —$NR_7COR_6$—, or $NR_7COOR_6$-substituted $C_6-C_{18}$aryl, $C_7-C_{18}$aralkyl or $A_5-A_{18}$heteroaryl, $R_6$ is hydrogen, is unsubstituted or mono- or poly-halogen-, -hydroxyl-, -oxo- or -cyano-substituted $C_1-C_{25}$alkyl or $C_2-C_{24}$alkenyl, which may be uninterrupted or interrupted one or more times by O, S or $NR_7$, or is unsubstituted or mono- or poly-halogen-, nitro-, -cyano-, -hydroxyl-, —$OR_7$—, —$SR_7$—, —$NR_7R_8$—, —$CONR_7R_8$—, —$COOR_7$—, —COOH— or $COO^-X^+$-substituted $C_6-C_{18}$aryl, $C_7-C_{18}$aralkyl or $A_5-A_{18}$heteroaryl, $R_7$ and $R_8$ independently of one another are hydrogen, $C_6-C_{18}$aryl, $C_7-C_{18}$aralkyl, unsubstituted or mono- or poly-halogen-, -hydroxyl- or —$C_1-C_{12}$alkoxy-substituted $C_1-C_{24}$alkyl or $C_2-C_{24}$alkenyl, or $R_7$ and $R_8$, together with the nitrogen, are unsubstituted or mono- to tetra-$C_1-C_4$alkyl-substituted pyrrolidine, piperidine, piperazine or morpholine, or are carbazole, phenoxazine or phenothiazine, $X^+$ is an alkali metal cation such as $Li^+$, $Na^+$, $K^+$ or alkaline earth metal cation such as $Mg^{++}_{1/2}$, $Ca^{++}_{1/2}$, $Sr^{++}_{1/2}$, $Ba^{++}_{1/2}$ or cations from group 11 of the IUPAC form of the periodic system such as $Cu^+$, $Cu^{++}_{1/2}$ or from group 12 of the IUPAC form of the periodic system such as $Zn^{++}_{1/2}$ or group 13 of the IUPAC form of the periodic system such as $Al^{+++}_{1/3}$, or an ammonium radical $[NR_7R_8R_{10}R_{11}]^+$, and $R_{10}$ and $R_{11}$ independently of one another are hydrogen, $C_1-C_{24}$alkyl, $C_5-C_{24}$aryl or $C_7-C_{25}$aralkyl.

In addition, processes for the preparation of compounds of formula (I), and also their use, have been found.

Alkyl, alkenyl or alkylene may be straight-chained or branched. $C_1-C_{24}$Alkyl is therefore for example with very particular preference $C_1-C_4$alkyl, such as methyl, ethyl, n-propyl, isopropyl, n-butyl, sec-butyl, isobutyl, tert-butyl, cyclobutyl, with particular preference $C_1-C_6$alkyl which corresponds to the definition given for $C_1-C_4$alkyl, and additionally n-pentyl, 2-pentyl, 3-pentyl, 2,2'-dimethylpropyl, cyclopentyl, cyclohexyl, n-hexyl, and preferably $C_1-C_8$alkyl, which corresponds to the definition given for $C_1-C_6$alkyl, and additionally n-octyl, 1,1',3,3'-tetramethylbutyl, 2-ethylhexyl, and especially $C_1-C_{12}$alkyl, which corresponds to the definition given for $C_1-C_8$alkyl, and additionally trimethylcyclohexyl, decyl, menthyl, thujyl, bornyl, 1-adamantyl, 2-adamantyl or dodecyl, and also $C_1-C_{15}$alkyl, which corresponds to the definition given for $C_1-C_{12}$alkyl, and additionally pentadecyl or tetradecyl, and also hexadecyl, heptadecyl, octadecyl, eicosyl, heneicosyl, docosyl or tetracosyl.

$C_1-C_{24}$Alkylene is therefore for example methylene, ethylene, n-propylene, isopropylene, n-butylene, sec-butylene, isobutylene, tert-butylene, cyclobutylene, n-pentylene, 2-pentylene, 3-pentylene, 2,2-dimethylpropylene, cyclopentylene, cyclohexylene, n-hexylene, n-octylene, 1,1,3,3-tetramethylbutylene, 2-ethylhexylene, nonylene, trimethylcyclohexylene, decylene, menthylene, thujylene, bornylene, 1-adamantylene, 2-adamantylene, dodecylene, tetradecylene, hexadecylene, heptadecylene, octadecylene, eicosylene, heneicosylene, docosylene or tetracosylene.

$C_2-C_{24}$Alkenyl is $C_2-C_{24}$alkyl and preferably $C_2-C_{12}$alkenyl, which is $C_2-C_{12}$alkyl which is mono- or polyunsaturated, it being possible for two or more double bonds to be present in isolation or in conjugation, where appropriate, for example vinyl, allyl, 2-propen-2-yl, 2-buten-1-yl, 3-buten-1-yl, 1,3-butadien-2-yl, 2-cyclobuten-1-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2-cyclopenten-1-yl, 2-cyclohexen-1-yl, 3-cyclohexen-1-yl, 2,4-cyclohexadien-1-yl, 2,5-hexadien-2-yl, 1-p-menthen-8-yl, 4(10)-thujen-10-yl, 2-norbornen-1-yl, 2,5-norbornadien-1-yl, 7,7-dimethyl-2,4-norcaradien-3-yl or the various isomers of hexenyl, octenyl, nonenyl, decenyl or dodecenyl.

$C_1-C_{24}$Alkoxy is O—$C_1-C_{24}$alkyl, preferably $C_1-C_6$alkoxy and with particular preference O—$C_1-C_4$alkyl, the alkyl radicals being as defined above.

$C_1-C_{24}$Alkylthio is S—$C_1-C_{24}$alkyl, preferably $C_1-C_6$alkylthio.

$C_1-C_5$Acyl is for example —CO-methyl, —CO-ethyl, —CO-propyl, —CO-isopropyl, —CO-sec-butyl, —CO-tert-butyl, —CO-n-butyl, —OCO-n-pentyl or —CO-sec-amyl, CO-tert-amyl.

O-interrupted $C_1-C_{12}$alkyl is for example $C_4$alkyl, such as especially —$CH_2$—$CH_2$—O—$CH_2$—$CH_2$—$CH_3$. Doubly O-interrupted $C_1-C_{12}$alkyl is for example $C_6$alkyl, such as especially —$CH_2$—$CH_2$—O—$CH_2$—$CH_2$—O—$CH_2$—$CH_3$. Oxo-substituted $C_1-C_{12}$alkyl is for example $C_2$alkyl, such as especially —C(=O)—$CH_3$. Oxo-substituted and O-interrupted $C_1-C_{12}$alkyl is for example $C_8$alkyl, such as especially —$(CH_2)_3C(=O)$—$C(CH_3)_3$, —C(=O)—$CH_2)_6$—$OCH_3$ or —$C(CH_3)_2$—COO—$(CH_2)_3$—$CH_3$.

O-interrupted $C_1-C_{24}$alkylene is for example $C_4$alkylene, such as especially —$CH_2$—$CH_2$—$CH_2$—$CH_2$—. Doubly O-interrupted $C_1-C_{24}$alkylene is for example $C_6$alkylene, such as especially —$CH_2$—$CH_2$—O—$CH_2$—$CH_2$—O—

CH$_2$—CH$_3$. Oxo-substituted C$_1$–C$_{24}$alkylene is for example C$_2$alkylene, such as especially —C(=O)—CH$_2$. Oxo-substituted and O-interrupted C$_1$–C$_{24}$alkylene is for example C$_8$alkylene, such as especially —(CH$_2$)$_3$—O—C(=O)—C(CH$_3$)$_3$, —C(=O)—CH$_2$)$_6$—OCH$_2$— or —C(CH$_3$)$_2$—COO—(CH$_2$)$_3$—CH$_2$—. Single or multiple substitution by halogen, hydroxyl, oxo or cyano, and single or multiple interruption by O, S or N, generally alter the chemical reactivity of an alkyl, alkenyl or alkylenyl group only slightly. The person skilled in the art will therefore readily recognize further possibilities for variation.

C$_5$–C$_{12}$Cycloalkyl is for example cyclopentyl, cyclohexyl, cycloheptyl or cyclooctyl, preferably C$_5$–C$_6$cycloalkyl such as cyclopentyl or cyclohexyl.

C$_5$–C$_{12}$Cycloalkylene is for example cyclopentylene, cyclohexylene, cycloheptylene, cyclooctylene or cyclododecylene such as 2-cyclopenten-1-yl, 2-cyclohexen-1-yl, 3-cyclohexen-1-yl, 2,4-cyclohexadien-1-yl and also 1-p-menthen-8-yl, 4(10)-thujen-10-yl, 2-norbornen-1-yl, 2,5-norbornadien-1-yl, 7,7-dimethyl-2,4-norcaradien-3-yl, preferably C$_5$–C$_6$cycloalkylene such as cyclopentylene or cyclohexylene.

Cycloalkyl or cycloalkylene may also be interrupted by heteroatoms such as for example —NH—, —S—, or units such as —CO—, —CONH$_2$, —CONH, —NH$_2$CO—, —COO— or —OCO—, and is for example piperazinyl or piperazinylene, tetrahydrofuryl, tetrahydropyrryl, 2-pyrrolidonyl, thiolanyl, oxazolanyl, tetrahydroimidazolyl, tetrahydrothiazole, piperidinyl, dioxanyl.

C$_5$–C$_{12}$Cycloalkoxy is O—C$_5$–C$_{12}$cycloalkyl, preferably C$_5$–C$_8$cycloalkyl, the cycloalkyl radicals being as defined above.

C$_5$–C$_{12}$Cycloalkylthio is S—C$_5$–C$_{12}$cycloalkyl, preferably C$_5$–C$_8$cycloalkyl, the cycloalkyl radicals being as defined above.

Cycloalkyl or cycloalkylene may also be interrupted by heteroatoms such as for example —NH—, —S—, or units such as —CO—, —CONH$_2$, —NH$_2$CO, —COO or —OCO— and is for example piperazinyl or piperazinylene.

A polycycle that may be interrupted by heteroatoms such as O, N, S or P is for example an aromatic, aliphatic or aromatic and aliphatic polycycle such as polyethers, for example a crownether, and also polyamines or polythioethers, or for example octahydroquinolizine or tetradecahydroacridine. The following may be mentioned by way of example as mono- or polycyclic alkenyl radicals:

Preferred aralkyl and aryl is C$_6$–C$_{12}$aralkyl or C$_6$–C$_{12}$aryl.

C$_7$–C$_{25}$Aralkyl is for example benzyl, 2-benzyl-2-propyl, β-phenylethyl, α,α-dimethylbenzyl, ω-phenylbutyl, ω,ω-dimethyl-ω-phenylbutyl, ω-phenyldodecyl, ω-phenyloctadecyl, ω-phenyleicosyl or ω-phenyldocosyl, preferably C$_7$–C$_{18}$aralkyl such as benzyl, 2-benzyl-2-propyl, β-phenylethyl, α,α-dimethylbenzyl, ω-phenylbutyl, ω,ω-dimethyl-ω-phenylbutyl, ω-phenyldodecyl or ω-phenyloctadecyl, and with particular preference for C$_7$–C$_{12}$aralkyl such as benzyl, 2-benzyl-2-propyl, β-phenylethyl, α,α-dimethylbenzyl, ω-phenylbutyl, ω,ω-dimethyl-ω-phenylbutyl or ω-phenyldodecyl.

C$_6$–C$_{12}$Aralkyl is for example benzyl, 2-benzyl-2-propyl, β-phenylethyl, 9-fluorenyl, α,α-dimethylbenzyl, ω-phenylbutyl or ω,ω-dimethyl-ω-phenylbutyl.

C$_6$–C$_{24}$Aryl is for example phenyl, 1-naphthyl, 2-naphthyl, 4-biphenylyl, phenanthryl, 2- or 9-fluorenyl or anthracenyl, preferably C$_6$–C$_{12}$aryl such as phenyl, 1-naphthyl, 2-naphthyl, 4-biphenylyl.

C$_6$–C$_{12}$Aryl is for example phenyl, 1-naphthyl, 2-naphthyl, 4-biphenylyl or 2-fluorenyl.

C$_6$–C$_{24}$Aryloxy is O—C$_6$–C$_{24}$aryl preferably C$_6$–C$_{12}$aryl, the aryl radicals being as defined above.

C$_6$–C$_{24}$Arylthio is S—C$_6$–C$_{24}$aryl, preferably C$_8$–C$_{12}$aryl, the aryl radicals being as defined above.

C$_6$–C$_{24}$Arylene is for example phenylene, 1-naphthylene, 2-naphthylene, 4-biphenylene, phenanthrylene, 2- or 9-fluorenylene or anthracenylene, preferably C$_6$–C$_{12}$arylene such as phenylene, 1-naphthylene, 2-naphthylene or 4-biphenylene.

Bi(C$_6$–C$_{24}$)arylene is preferably biphenylene, 4- or 3-biphenylene.

A$_5$–A$_{18}$Heteroaryl is a polyunsaturated heterocyclic framework of 5 to 18 atoms, selected from C, N, O and S, which includes at least 6 conjugated π electrons. For example, A$_5$–A$_{18}$heteroaryl is thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythiinyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, preferably mono- and bicyclic heteroaromatic radicals.

A$_5$–A$_{18}$Heteroaryloxy is O—A$_5$–A$_{18}$heteroaryl, the heteroaryl radicals being as defined above.

A$_5$–A$_{18}$Heteroarylthio is S—A$_5$–A$_{18}$heteroaryl, the heteroaryl radicals being as defined above.

A$_5$–A$_{18}$Heteroaryl is a polyunsaturated heterocyclic framework of 5 to 18 atoms, selected from C, N, O and S, that includes at least 6 conjugated π electrons. For example, A$_5$–A$_{18}$heteroarylene is thienylene, benzo[b]thienylene, dibenzo[b,d]thienylene, thianthrenylene, furylene, furfurylene, 2H-pyranylene, benzofuranylene, isobenzofuranylene, dibenzofuranylene, phenoxythiinylene, pyrrolylene, imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, quinolylene, isoquinolylene, phthalazinylene, naphthyridinylene, quinoxalinylene, quinazolinylene, cinnolinylene, pteridinylene, carbazolylene, carbolinylene, benzotriazolylene, benzoxazolylene, phenanthridinylene, acridinylene, perimidinylene, phenanthrolinylene, phenazinylene, isothiazolylene, phenothiazinylene, isoxazolylene, furazanylene or phenoxazinylene, preferably mono- and bicyclic heteroaromatic radicals.

Bi(A$_5$–A$_{18}$)heteroarylene is preferably by pyridylene.

Halogen is chlorine, bromine, fluorine or iodine, preferably fluorine or chlorine.

Mono- or poly-halogen-, -hydroxyl-, —C$_1$–C$_{12}$alkoxy- or -cyano-substituted C$_1$–C$_{12}$alkyl or C$_2$–C$_{12}$alkenyl is for example 2-chloroethyl, trifluoromethyl, pentafluoroethyl, β,β,β-trifluoroethyl, trichlorovinyl, ω-chloropropyl, ω-bromobutyl, perfluorohexyl, perfluorodocecyl, 2-hydroxyethyl, 2-methoxyethyl, 2-ethoxyethyl, 2-butoxyethyl, 2,3-dihydroxypropyl, 2,3-dimethoxypropyl, 2,3-dimethoxypropyl or 2-cyanoethyl, preferably trifluoromethyl, 2-hydroxyethyl, 2-methoxyethyl, 2-ethoxyethyl or 2-cyanoethyl.

One particularly preferred embodiment of the present invention relates to compounds of the formula (Ia), (Ib) or (Ic),
in which
$X_1$ is a compound selected from the group of the compounds of the formulae (III), (IV), (V), (VI), (VII) and (VIII)

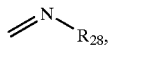  (III)

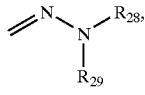  (IV)

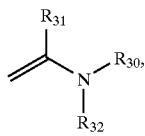  (V)

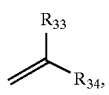  (VI)

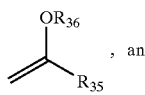  (VII)

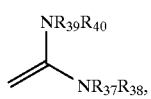  (VIII)

in which
$R_{28}$, $R_{29}$, $R_{33}$, $R_{34}$, $R_{35}$, $R_{36}$, $R_{37}$, $R_{38}$, $R_{39}$ and $R_{40}$ independently of one another are substituted or unsubstituted $C_1$–$C_{24}$alkyl, $C_1$–$C_{24}$alkoxy, $C_5$–$C_{12}$cycloalkyl, $C_2$–$C_{24}$alkenyl, $C_6$–$C_{24}$aryl, $C_5$–$C_{24}$aryloxy, $C_7$–$C_{25}$aralkyl, or $A_5$–$A_{18}$heteroaryl, and with particular preference are $C_6$–$C_{12}$aryl, $C_6$–$C_{12}$aralkyl or $A_5$–$A_8$heteroaryl, $A_5$–$A_{18}$heteroaryloxy, or dependently on one another are hydrogen, and
$R_{31}$ is hydrogen or —$NR_{89}R_{90}$, in which
$R_{89}$ and $R_{90}$ independently of one another possess the same definition as $R_{38}$ and $R_{40}$, or are $C_1$–$C_{24}$alkyl, $C_1$–$C_{24}$alkylthio, $C_5$–$C_{12}$cycloalkoxy, $C_5$–$C_{12}$cycloalkylthio, $C_5$–$C_{24}$aryloxy, -thio or $A_5$–$A_{18}$heteroaryloxy, -thio, and
$R_{30}$ and $R_{32}$ are hydrogen, or independently of one another are $C_6$–$C_{24}$aryl-substituted primary or secondary amine or $C_6$–$C_{24}$aryl, with the proviso that $R_3$ is not hydrogen, methoxy or hydroxyl, or
$R_{33}$ and $R_{34}$ together are a lactam, barbituric acid or isoindoline radical, and
$X_2$ is a compound selected from the group of the compounds of the formulae (IX), (X), (XI), (XII), (XIII) and (XIV)

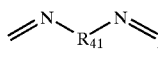  (IX)

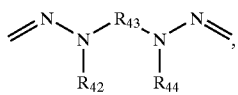  (X)

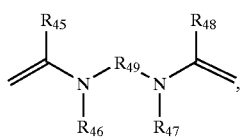  (XI)

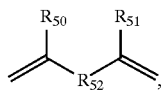  (XII)

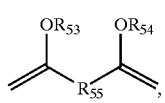  (XIII)

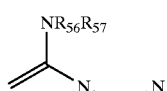  (XIV)

in which
$R_{42}$, $R_{44}$, $R_{46}$, $R_{47}$, $R_{50}$, $R_{51}$, $R_{53}$, $R_{54}$, $R_{56}$, $R_{57}$, $R_{58}$, $R_{60}$, $R_{61}$ and $R_{62}$ independently of one another are substituted or unsubstituted $C_1$–$C_{24}$alkyl, $C_6$–$C_{12}$cycloalkyl, $C_2$–$C_{24}$alkenyl, $C_6$–$C_{24}$aryl, $C_6$–$C_{25}$aralkyl or $A_5$–$A_{18}$heteroaryl, and with particular preference are $C_6$–$C_{12}$aryl, $C_7$–$C_{12}$aralkyl or $A_5$–$A_6$heteroaryl, or dependently of one another are hydrogen, and
$R_{45}$ and $R_{48}$ independently of one another are hydrogen, $C_1$–$C_{24}$alkyl, $C_1$–$C_{24}$alkoxy, $C_1$–$C_{24}$alkylthio, $C_5$–$C_{12}$cycloalkyl, $C_5$–$C_{12}$cycloalkoxy, $C_5$–$C_{12}$cycloalkylthio, $C_2$–$C_{24}$alkenyl, $C_5$–$C_{24}$aryl, $C_7$–$C_{25}$aralkyl, $C_5$–$C_{24}$aryloxy, -thio or $A_5$–$A_{18}$heteroaryl, $A_5$–$A_{18}$heteroaryloxy, -thio, and
$R_{41}$, $R_{43}$, $R_{49}$ and $R_{59}$ are $C_6$–$C_{24}$arylene, $A_5$–$A_{18}$heteroarylene, $C_5$–$C_{12}$cycloalkylene or bi($C_8$–$C_{24}$)arylene, bi($A_5$–$A_{18}$)heteroarylene, in which the bi compounds are connected to one another by a direct bond or by one or more intermediate units such as —CH=CH—, —CH=N—, —N=N—, —$CR_{43}R_{44}$—, —CO—, —COO—, —OCO—, —$NR_{43}$CO—, —$CONR_{43}$—, —O—, —S—, —SO—, —$SO_2$— or —$NR_{44}$—, or are $C_2$–$C_{24}$alkenylene which may be interrupted one or more times by —CH=N—, —N=N—, —$CR_{43}R_{44}$—, —CO—, —COO—, —OCO—, —$NR_{43}$CO—, —$CONR_{43}$—, —O—, —S—, —SO—, —$SO_2$— or —$NR_{44}$— units, or
$R_{41}$ is a direct bond, and
$R_{52}$ and $R_{55}$ are $A_5$–$A_{18}$heteroarylene, or 1,2- or 1,3-phenylene, substituted 1,4-phenylene, or polyether, polyimine, polyamine, or bi($C_6$–$C_{24}$)arylene or bi($A_5$–$A_{18}$)heteroarylene, which are connected to one another directly or via —C—, —N—, —O—, or a (—N=N—) unit.

Another preferred embodiment of the present invention relates to compounds of the formula (XVI)

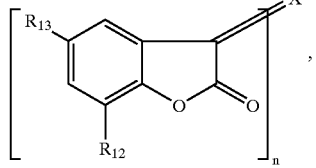  (XVI)

in which
n is 1 or 2, and
if n is 1
X is $X_1$ of formula (Ia), and if n is 2

X is $X_2$ of formula (Ib) or (Ic), and $R_{12}$ and $R_{13}$ independently of one another are hydrogen, halogen, $NO_2$, $R_{14}$, $(C_1-C_{12}alkyl)$-$COOR_5$, $OR_{14}$, $SR_{14}$, $OC_9-C_{18}alkyl$ or $SC_9-C_{18}alkyl$, in which $R_{14}$ is $C_1-C_{12}alkyl$ which is unsubstituted or substituted one or more times by oxo, cyano or $COO^-X_5$, and which may be uninterrupted or interrupted one or more times by O, or $R_{14}$ is $C_7-C_{18}aralkyl$ or $C_6-C_{12}aryl$ which is unsubstituted or substituted one or more times by halogen, nitrogen, cyano, $OR_{16}$, $NR_{16}R_{17}$, $CONR_{16}R_{17}$, $NR_{18}COR_{16}$ or $NR_{18}COOR_{16}$, $X_5^+$ is a cation $Na^+$, $K^+$, $Mg^{++}{}_{1/2}$, $Ca^{++}{}_{1/2}$, $Zn^{++}{}_{1/2}$, $Al^{+++}{}_{1/3}$, or $[NR_{16}R_{17}R_{18}R_{19}]^+$, and $R_{16}$ and $R_{17}$ independently of one another are hydrogen, $C_6-C_{12}aryl$, $C_7-C_{10}aralkyl$, or $C_1-C_8alkyl$ which is unsubstituted or substituted one or more times by halogen, hydroxyl or $C_1-C_4alkoxy$, or $R_{16}$ and $R_{17}$, together with the conjoint N, are pyrrolidine, piperidine, piperazine or morpholine, each of which is unsubstituted or substituted one or more times by $C_1-C_4alkyl$, and $R_{18}$ and $R_{19}$ independently of one another are hydrogen, $C_1-C_8alkyl$, $C_6-C_{10}aryl$ or $C_6-C_{12}aralkyl$.

With very particular preference, $R_{12}$ and $R_{13}$ independently of one another are hydrogen, chloro, $R_{22}$, $C_2H_5$—COOH, $C_2H_5$—$COO(C_1-C_{12}alkyl)$, $OR_{22}$, $SR_{22}$, $OC_9-C_{18}alkyl$ or $SC_9-C_{18}alkyl$, in which $R_{22}$ is $C_1-C_8alkyl$ which is unsubstituted or substituted one or more times by oxo, cyano or $COO^-X_6^+$ and which may be uninterrupted or interrupted one or more times by O, or $R_{22}$ is $C_6-C_{12}aryl$ or $C_7-C_{12}aralkyl$, $X_6^+$ is an alkali metal cation such as $Na^+$, $K^+$ or alkaline earth metal cation such as $Mg^+{}_{1/2}$, $Ca^{++}{}_{1/2}$, or cations from group 12 of the IUPAC form of the periodic system such as $Zn^{++}{}_{1/2}$ or group 13 of the IUPAC form of the periodic system such as $Al^{++}{}_{1/3}$, or an ammonium radical $[NR_7R_8R_{10}R_{11}]^+$, $R_{24}$, $R_{25}$ and $R_{26}$ independently of one another are $C_1-C_4alkyl$ or phenyl, and $R_{27}$ is H, $C_1-C_8alkyl$, $C_6-C_{12}aryl$ or $C_7-C_{12}aralkyl$.

With very particular preference, especially, $R_{12}$ is tert-butyl and $R_{13}$ is tert-butyl, $OCH_3$, $CH_2CH_2COOH$ or $CH_2CH_2COO(C_1-C_{12}alkyl)$.

One particularly preferred embodiment of the present invention relates to compounds of the formulae (Ia), (Ib) or (Ic) in which $X_1$ is a hydrazone radical of the formula (IV) and $X_2$ is a compound of the formulae (X), especially =N—$NR_{63}R_{64}$, and with very particular preference a compound of the formula (XVII)

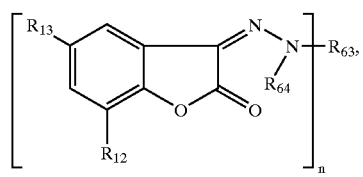

(XVII)

in which if n is 1

$R_{64}$ independently of $R_{63}$ possesses the same definition as $R_{63}$ and additionally is hydrogen, and $R_{63}$ is substituted or unsubstituted $C_1-C_{24}alkyl$, $C_5-C_{12}cycloalkyl$, $C_2-C_{24}alkenyl$, $C_6-C_{24}aryl$, $C_7-C_{25}aralkyl$, or $A_5-A_{18}heteroaryl$, and with particular preference is $C_6-C_{12}aryl$, $C_7-C_{12}aralkyl$ or $A_5-A_8heteroaryl$ and dependently on the other radicals is hydrogen, with the proviso that in formula (XVII) $R_{12}$ or $R_{13}$ are not hydrogen and/or methyl, and with very particular preference is a compound selected from the group of the compounds of the formulae (XVIII), (IXX), (XX) and (XXI)

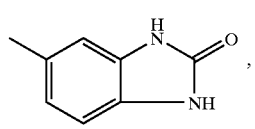

(XVIII)

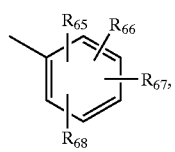

(IXX)

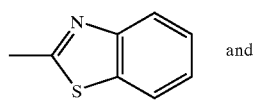

(XX)

and

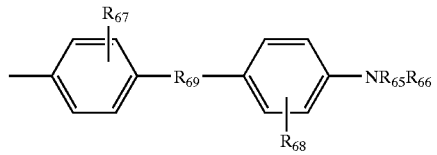

(XXI)

in which $R_{65}$ and $R_{66}$ independently of one another are hydrogen, $C_1-C_{24}alkyl$, especially methyl, ethyl, propyl, isopropyl, n-butyl, isobutyl, sec-butyl, tert-butyl, n-pentyl, sec-amyl, tert-amyl, hexyl or 2,2-dimethylbutyl, or additionally are $C_5-C_6cycloalkyl$, unsubstituted phenyl or $R_{67}$-substituted phenyl, $R_{68}$ independently of $R_{67}$ possesses the same definition as $R_{67}$, and $R_{69}$ is a direct bond, —$CH_2$—, —$CH(CH_3)$—, —$C(CH_3)_2$—, —CH=N—, —N=N—, —O—, —S—, —SO—, —$SO_2$— or —$NR_{65}$—, $R_{67}$ is hydrogen, nitro, cyano, halogen such as F, Cl, Br, I or $C_1-C_8alkyl$, $C_1-C_8alkoxy$, unsubstituted or $NR_{65}R_{66}$-substituted $C_5-C_6cycloalkyl$, and preferably nitro, chloro, $C_1-C_6alkyl$ or $C_1-C_6alkoxy$, and if n is 2

$R_{63}$ is a bridge to a further benzofuran-2-one (XVII), the said bridge being $C_8-C_{24}arylene$, $A_5-A_{18}heteroarylene$, $C_5-C_{12}cycloalkylene$ or polymethylidene, -ether, -imines, -amines, or bi-$C_6-C_{24}arylene$ or bi($A_5-A_{16}$) heteroarylene, which are connected to one another directly or via —C—, —N—, —O—, or a (—N=N—) unit, and with particular preference is a compound selected from the group of the compounds of the formula (XXII) and (XXIII)

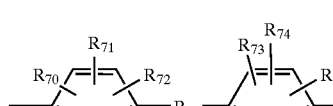

(XXII)

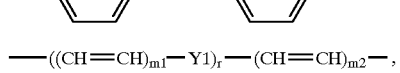

(XXIII)

in which $R_{70}$, $R_{71}$, $R_{72}$, $R_{73}$, $R_{74}$ and $R_{75}$ independently of one another correspond to the definition of $R_{65}$, and with particular preference at least two of $R_{70}$, $R_{71}$, $R_{72}$, $R_{73}$, $R_{74}$ or $R_{75}$ are independently of one another hydrogen, and $R_{76}$ is a direct bond or is one or more —CH=N—, —N=N—, —$CR_{45}R_{48}$—, —CO—, —COO—, —OCO—, —$NR_{46}$CO—, —$CONR_{46}$—, —O—, —S—, —SO—, —$SO_2$— or —$NR_{46}$-units, and with very particular preference is a direct bond, and Y1 is a direct bond or $C_6$–$C_{24}$arylene, such as substituted or unsubstituted phenylene, especially 1,4-phenylene which is unsubstituted or substituted one or more times by halogen, nitro, cyano or amine, or is $A_5$–$A_{18}$heteroarylene, $C_5$–$C_{12}$cycloalkylene, such as especially cyclohexylene or piperazinylene, and also bi($C_6$–$C_{24}$)arylene, especially substituted or unsubstituted biphenylene, or bi($A_5$–$A_{18}$)heteroarylene, or is —CH=N—, —N=N—, —$CR_{74}R_{75}$—, —CO—, —COO—, —OCO—, —$NR_{65}$CO—, —$CONR_{65}$—, —O—, —S—, —SO—, —$SO_2$— or —$NR_{65}$-units, and r is an integer from 0 to 10, and preferably is 0, 1 or 2, and m1 and m2 are an integer from 0 to 10, and preferably are 1 or 2, with the proviso that in formula (XVII) $R_{12}$ or $R_{13}$ are not hydrogen and/or methyl.

Another particularly preferred embodiment of the present invention relates to compounds of the formulae (Ia), (Ib), or (Ic) in which $X_1$ is an imine radical of the formula (III) and $X_2$ is a compound of the formulae (IX), especially =$NR_{77}$ and with very particular preference a compound of the formula (XXIV)

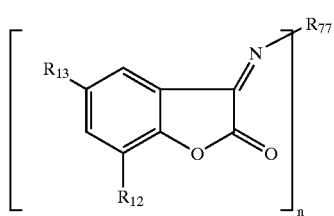

(XXIV)

in which $R_{77}$ possesses the same definition as $R_{63}$, and if n is 1 with very particular preference is a compound of the formula (IXX), with the proviso that in formula (XXIV), if $R_{12}$ or $R_{13}$ is hydrogen, the unsubstituted phenylimine and also 4-dimethylamine-phenylimine radical is excluded.

The present invention furthermore provides with particular preference compounds of the formulae (Ia), (Ib) or (Ic) in which $X_1$ is a compound of the formulae (V) or (VIII) and $X_2$ is a compound of the formulae (XI) or (XIV), especially =$C(R_{80})$—$NR_{78}R_{79}$ and with very particular preference a compound of the formula (XXV)

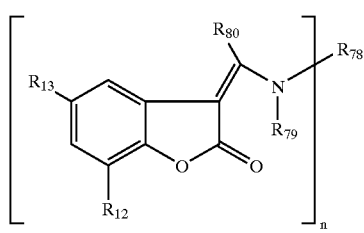

(XXV)

in which if n is 1

$R_{78}$ and $R_{79}$ independently of one another possess the same definition and are hydrogen, or independently of one another are $C_6$–$C_{24}$aryl-substituted primary or secondary amine or $C_6$–$C_{24}$aryl, with the proviso that $R_{13}$ is not hydrogen, methoxy or hydroxyl, and with very particular preference, if n is 1, are independently of one another a compound of the formula (IXX) or hydrogen, and in n is 2 possess independently of one another the same definition as $R_{63}$, and $R_{80}$ is hydrogen or —$NR_{89}R_{90}$, in which $R_{89}$ and $R_{90}$ independently of one another are substituted or unsubstituted $C_1$–$C_{24}$alkyl, $C_1$–$C_{24}$alkoxy, $C_1$–$C_{24}$alkylthio, $C_5$–$C_{12}$cycloalkoxy, $C_5$–$C_{12}$cycloalkylthio, $C_6$–$C_{24}$aryloxy, -thio or $A_5$–$A_{18}$-heteroaryloxy, -thio, $C_5$–$C_{12}$cycloalkyl, $C_2$–$C_{24}$alkenyl, $C_6$–$C_{24}$aryl, $C_7$–$C_{25}$aralkyl, or $A_5$–$A_8$heteroaryl, and with particular preference are $C_6$–$C_{12}$aryl, $C_6$–$C_{12}$aralkyl or $A_5$–$A_8$heteroaryl, or dependently on one another are hydrogen, and with particular preference are hydrogen or a compound of the formula (IXX), with the proviso that $R_{13}$ is not hydrogen, methoxy or hydroxyl.

Furthermore, in one particularly preferred embodiment, the present invention provides compounds of the formulae (Ia), (Ib) or (Ic), in which $X_1$ is a compound of the formulae (VI) or (VII) and $X_2$ is a compound of the formulae (XII) or (XIII), especially =$C(R_{81})$—$R_{82}$, and with very particular preference a compound of the formula (XXXVI)

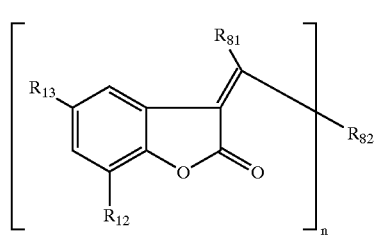

(XXVI)

in which if n is 1

$R_{81}$ and $R_{82}$ are $C_6$–$C_{24}$aryl, if $R_{12}$ or $R_{13}$ are not hydrogen, or independently of one another are unsubstituted or substituted ($C_8$–$C_{24}$aryl)oxy and hydrogen, $C_1$–$C_{24}$alkyl, $C_1$–$C_{24}$alkoxy, $C_1$–$C_{24}$alkylthio radical, $C_5$–$C_{12}$cycloalkyl, $C_5$–$C_{12}$cycloalkoxy, $C_5$–$C_{12}$cycloalkylthio radical, $C_2$–$C_{24}$alkenyl, $C_2$–$C_{24}$aryl, $C_6$–$C_{24}$aryloxy, -thio or $A_5$–$A_{18}$heteroaryl, -thio, and with particular preference are $C_5$–$C_{24}$aryloxy, $C_1$–$C_{24}$alkoxy, $C_5$–$C_{12}$cycloalkoxy, or $R_{81}$ and $R_{82}$ together are a lactam, barbituric acid or isoindoline radical of the formulae (XXVII), (XXVIII) or (IXXX)

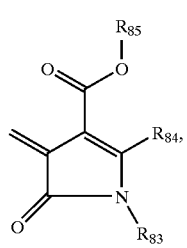

(XXVII)

(XXVIII)

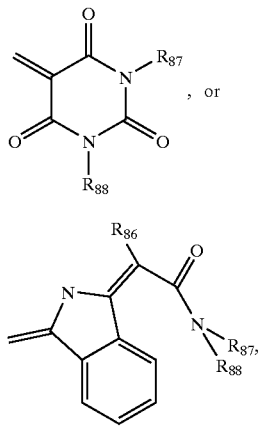

(IXXX)

in which

R$_{83}$, R$_{85}$, R$_{87}$ and R$_{88}$ independently of one another are substituted or unsubstituted C$_1$–C$_{24}$alkyl, C$_5$–C$_{12}$cycloalkyl, C$_2$–C$_{24}$alkenyl, C$_6$–C$_{24}$aryl, C$_6$–C$_{25}$aralkyl, or A$_5$–A$_{18}$heteroaryl, and with particular preference are C$_6$–C$_{12}$aryl, C$_7$–C$_{12}$aralkyl or A$_5$–A$_8$heteroaryl, or dependently on one another are hydrogen, and R$_{86}$ is hydrogen, C$_1$–C$_{24}$alkyl, C$_1$–C$_{24}$alkoxy, C$_1$–C$_{24}$alkylthio, C$_5$–C$_{12}$cycloalkyl, C$_5$–C$_{12}$cycloalkoxy, C$_5$–C$_{12}$cycloalkylthio, C$_2$–C$_{24}$alkenyl, C$_5$–C$_{24}$aryl or C$_7$–C$_{25}$aralkyl, and if n is 2

R$_{82}$ is a bridge to a further benzofuran-2-one of the formula (XXVI), in which the bridge is (A$_5$–A$_{18}$)heteroarylene, or 1,2- or 1,3-phenylene, substituted 1,4-phenylene, or polyether, polyimine, polyamine, or bi(C$_6$–C$_{24}$)arylene or bi(A$_5$–A$_{18}$)heteroarylene, which are connected to one another directly or via —C—, —N—, —O—, or a (—N=N—) unit, with the proviso that R$_{81}$ and R$_{82}$ are not methyl and —OCO-4-(1-chlorophenylene), and, if R$_{12}$ or R$_{13}$ are hydrogen, R$_{81}$ and R$_{82}$ are not phenyl.

The compounds of the formula (I) of the invention are generally obtained by C—H-acidic coupling reaction of a benzofuran-2-one with a compound capable of coupling, in the presence of an acidic or basic catalyst (in analogy to Organikum, 19th Edition 1993, pp. 459–495).

The present invention accordingly likewise provides a process for preparing the benzofuran-2-ones (Ia) by reacting benzofuran-2-one (XXXa)

(XXXa)

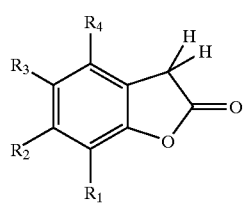

with a compound of the formulae (XXXIa), (XXXIIa), (XXXIIIa), (XXXIVa) or (XXXVa)

XXXIa

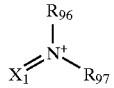

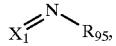 XXXIIa

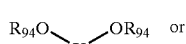 XXXIIIa

R$_{94}$O$_{\diagdown}$X$_1$$_{\diagup}$OR$_{94}$ or  XXXIVa

XXXVa

R$_{96}$
|
X$_1^{=}$N$^+$$_{\diagdown}$R$_{97}$ in which

Hal is halogen, and

R$_{94}$ possesses the same definition as R$_{36}$, and

R$_{95}$ is C$_6$–C$_{12}$aryl, especially phenyl,

R$_{96}$ and R$_{97}$ independently of one another are C$_6$–C$_{12}$aryl, especially phenyl, or are C$_1$–C$_5$acyl, C$_6$–C$_{12}$aralkyl, C$_1$–C$_4$alkyl, and R$_{96}$ and R$_{97}$ are in particular methyl, or phenyl and CH$_3$CO, or phenyl and methyl.

The reaction is normally started by contacting benzofuran-2-one (XXXa) with a compound of the formulae (XXXIa), (XXXIIa), (XXXIIIa), (XXXIVa) or (XXXVa) in accordance with methods which are known per se, for example by mixing the starting products or by adding one starting product dropwise to the other.

In general the chosen molar ratio of a compound (XXXa) to a compound of the formulae (XXXIa), (XXXIa), (XXXIIIa), (XXXIVa) or (XXXVa) is in the range from 0.8:1 to 3:1; preferably, the molar ratio is situated within the range from 0.9:1 to 2:1.

If desired, the reaction may be conducted in an organic solvent or in a melt; preferably, the reaction is conducted in a solvent.

The chosen molar ratio of organic solvent to the compound (XXXa) is generally in the range from 500:1 to 1:2, preferably from 100:1 to 1:1.

The chosen reaction temperature is commonly in the range from −20 to 250° C., preferably from 0 to 200° C.; preferably, the chosen reaction temperature is a temperature at which the reaction mixture boils and is situated in the range of the boiling temperature of the solvent used.

The pressure chosen is preferably atmospheric pressure.

The reaction time is normally chosen as a function of the reactivity of the starting products and of the chosen temperature, and is generally in the range from 10 minutes to 48 hours.

If desired, the reaction may be conducted in the presence of a catalyst.

In general, the chosen molar ratio of the catalyst to the compound of the formulae (XXXIa), (XXXIIa), (XXXIIIa), (XXXIVa) or (XXXVa) is in the range from 0.001:1 to 5:1, preferably in the range from 0.001:1 to 1:1.

Both acidic and basic catalysts are suitable.

Examples of acidic catalysts which may be used include inorganic acids, such as hydrochloric, phosphoric, hydrobromic or sulfuric acid, or zinc chloride, aluminium chloride or boron trifluoride, or organic acids or alkyl acids such as formic, acetic, propionic, chloroacetic or trifluoroacetic acid, or sulfonic acids such as arylsulfonic acids such as p-toluene- or methanesulfonic add or silicates such as Fulkat 40 (Pontecchio Marconi), Katalysator K10 (Süd-Chemie) or Katalysator Rudex (Rudex Nebelova Bratislava).

Examples of suitable basic catalysts are organic amines such as triethylamine, dialkylamine, piperidine, pyrrolidine, pyridine, morpholine, N,N'-dimethylaniline, or aliphatic alkoxides, such as sodium methoxide, ethoxide, propoxide or butoxide or potassium tert-butoxide, for example, or aromatic alkoxides such as phenoxide, for example, or carboxylic salts such as sodium or potassium acetate, for example, or alkali metal or alkaline earth metal oxides, hydroxides, hydrides or carbonates, such as sodium or potassium hydroxide, sodium or potassium hydride, calcium oxide, magnesium oxide, sodium carbonate, potassium carbonate, sodium hydrogen carbonate, for example, or ammonia or tetrabutylammonium hydroxide.

Chosen solvents are generally organic solvents, especially inert organic solvents, for example ethers such as tetrahydrofuran, dioxane, diethyl ether, methyl tert-butyl ether, glycols and their ethers such as mono-, di-, tri-, tetraethylene glycol, propylene glycol, their methyl, ethyl, butyl ethers, or $C_5$–$C_{12}$alkanes such as pentane, hexane, heptane, octane, nonane, decane, undecane, dodecane or $C_5$–$C_{12}$cycloalkanes such as cyclopentane, cyclohexane, cycloheptane, cyclooctane, cyclononane, cyclodecane or cyclododecane or, in particular, halogenated alkanes such as dichloromethane, dichloroethane, trichloromethane, tetrachloromethane, dichloroethylene, trichloroethane or tetrachloroethane, or aryls such as benzene, toluene, or xylene, chloro-, dichloro-, trichlorobenzene, or alcohols such as methanol, ethanol, propanol, sec-propanol, butanol or carboxylic acids such as formic acid, acetic acid, propionic acid or esters such as ethyl acetate, polar aprotic solvents such as N,N-dimethylformamide, N-methylpyrrolidine, dimethylacetamide or dimethyl sulfoxide.

Furthermore, with particular preference the reaction is conducted in an inert gas atmosphere. Inert gases that can be used include noble gases, preferably helium and argon, and nitrogen.

It is found to be advantageous in the process of the invention to use additions of binding agents such as anhydrides, especially acetic anhydride, or to use physical methods, such as distillation, for example, to remove leaving groups that are formed.

The molar ratio of anhydride to the compound of the formulae (XXXIa), (XXXIIa), (XXXIIIa), (XXXIVa) or (XXXVa) is in the range from 0.1:1 to 5:1, preferably in the range from 0.5:1 to 2:1.

The product may be isolated by the customary methods, such as by filtration, for example, and, if desired, subsequently washing of the filter residue with, for example, water and/or an organic solvent such as methanol, and drying of the moist filter residue.

Normally, for example, the organic phase, comprising the reaction product, is washed with water and the organic phase is subsequently concentrated, preferably to dryness. In a further variant of working up, the organic reaction product may also be concentrated by evaporation directly and then purified by means, for example, of recrystallization or column-chromatographic separation. In the case of recrystallization, isolation is normally done by filtration and subsequent washing of the filter residue with, preferably, a solvent in which the reaction product is poorly soluble. The column-chromatographed organic phase comprising the reaction product may be concentrated by evaporation directly. If desired, the reaction products may be dried after isolation. This is generally done using conventional drying apparatus such as drying ovens or paddle dryers.

In the process of the invention it has proven to be advantageous to work up the product by adding, for example, water and/or acid and then subjecting the crude product to extraction with an organic solvent, such as toluene. In general, the organic phase, comprising the crude product, is washed with water and then concentrated by evaporation. If desired, the crude product is subsequently recrystallized. In general, for this purpose, the crude product is admixed with an organic solvent such as methanol, for example, and the resulting mixture is heated to boiling. Normally, the boiling temperature is maintained until all of the product has dissolved. Thereafter the mixture is cooled, usually to a temperature in the range form −20 to 40° C., and filtered, the product being obtained as the filter residue. Normally, the filter residue is then dried in vacuo in the range from 40 to 200° C., preferably in the range from 60 to 120° C.

In addition, the present invention also provides a process for preparing the benzofuran-2-ones (Ib) or (Ic) by reacting benzofuran-2-one (XXXa), or (XXXa) and a compound of the formula (XXXb)

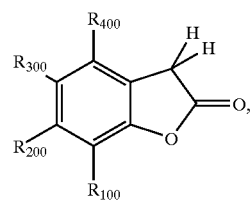

(XXXb)

with a compound of the formulae (XXXIb), (XXXIIb), (XXXIIIb), (XXXIVb) or (XXXVb)

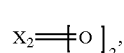

XXXIb

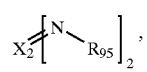

XXXIIb

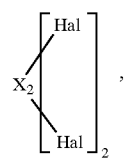

XXXIIIb

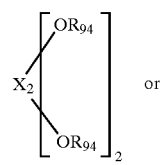

XXXIVb or

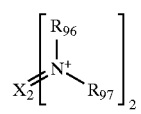

XXXVb

The reaction is normally started by contacting benzofuran-2-ones of the formula (XXXa), or (XXXa) and (XXXb), in analogy to known methods, with a compound of the formulae (XXXIb), (XXXIIb), (XXXIIIb), (XXXIVb) or (XXXVb), for example by mixing the starting components, or adding one starting product dropwise to the other, it being possible to react the benzofuran-2-ones (XXXa), or (XXXa) and (XXXb), in two portions or one portion.

In general, the molar ratio of a compound (XXXa), or (XXXa) and (XXXb), to a compound of the formulae (XXXIb), (XXXIIb), (XXXIIIb), (XXXIVb) or (XXXVb) is in the range from 1:0.9 to 1:0.2; preferably, the molar ratio is situated within the range from 1:0.6 to 1:0.4.

If desired, the reaction may be conducted in an organic solvent or in a melt; preferably, the reaction is conducted in a solvent.

The chosen molar ratio of organic solvent to the compound (XXXa), or (XXXa) and (XXXb), is generally in the range from 500:1 to 1:2, preferably from 100:1 to 1:1.

The chosen reaction temperature is normally in the range from −20 to 250° C., preferably from 0 to 200° C.; preferably, the chosen reaction temperature is a temperature at which the reaction mixture boils and is situated in the range of the boiling temperature of the solvent used.

The pressure chosen is preferably atmospheric pressure.

The reaction time is normally chosen as a function of the reactivity of the starting products and of the chosen temperature, and is generally in the range from 10 minutes to 48 hours.

If desired, the reaction may be conducted in the presence of a catalyst.

In general, the chosen molar ratio of the catalyst to the compound of the formulae (XXXIb), (XXXIIb), (XXXIIIb), (XXXIVb) or (XXXVb) is in the range from 0.001:1 to 5:1, preferably in the range from 0.001:1 to 1:1.

Both acidic and basic catalysts are suitable.

Catalysts, solvents, correspond to the definition given above.

Moreover, with particular preference the reaction is conducted in an inert gas atmosphere. Inert gases that can be used include noble gases, preferably helium and argon, and nitrogen.

It is found to be advantageous in the process of the invention to use additions of binding agents such as anhydrides, especially acetic anhydride, or to use physical methods, such as distillation, for example, to remove leaving groups that are formed.

The molar ratio of anhydride to the compound of the formulae (XXXIb), (XXXIIb), (XXXIIIb), (XXXIVb) or (XXXVb) is in the range from 0.1:1 to 5:1, preferably in the range from 0.5:1 to 2:1.

Working up and isolation are carried out as described above.

Moreover, the present invention also provides a process for preparing the benzofuran-2-ones (Ia) by reacting 3-oxobenzofuran-2-one (XXXVIa)

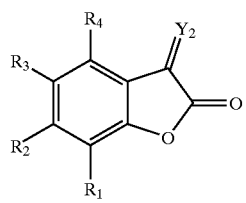

(XXXVIa)

with a compound of the formula (XXXVIa)

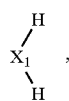

(XXXVIIa)

in which
$Y_2$ is O, $NR_{95}$ or $N^+(R_{96}R_{97})$, $CCl_2$ or NO.

The reaction is normally started by contacting benzofuran-2-one (XXXVIa) with a compound of the formula (XXXIa), (XXXIIa), (XXXIIIa), (XXXIVa) or (XXXVa) by methods which are known per se, for example by mixing the starting products, or by adding one starting product dropwise to the other.

In general, the chosen molar ratio of a compound (XXXVIa) to a compound of the formulae (XXXIa), (XXXIIa), (XXXIIIa), (XXXIVa) or (XXXVa) is in the range from 0.8:1 to 3:1; preferably, the molar ratio is situated within the range from 0.9:1 to 2:1.

If desired, the reaction may be conducted in an organic solvent or in a melt; preferably, the reaction is conducted in a solvent.

The chosen molar ratio of organic solvent to the compound (XXXVIa) is generally in the range from 500:1 to 1:2, preferably from 100:1 to 1:1.

The chosen reaction temperature is normally in the range from −20 to 250° C., preferably from 0 to 200° C.; preferably, the chosen reaction temperature is a temperature at which the reaction mixture boils and is situated in the range of the boiling temperature of the solvent used.

The pressure chosen is preferably atmospheric pressure.

The reaction time is normally chosen as a function of the reactivity of the starting products and of the chosen temperature, and is generally in the range from 10 minutes to 48 hours.

If desired, the reaction may be conducted in the presence of a catalyst.

In general, the chosen molar ratio of the catalyst to the compound of the formulae (XXXIa), (XXXIIa), (XXXIIIa), (XXXIVa) or (XXXVa) is in the range from 0.001:1 to 5:1, preferably in the range from 0.001:1 to 1:1.

Both acidic and basic catalysts are suitable.

Catalysts, solvents, correspond to the definition given above.

Moreover, with particular preference the reaction is conducted in an inert gas atmosphere. Inert gases that can be used include noble gases, preferably helium and argon, and nitrogen.

It is found to be advantageous in the process of the invention to use additions of binding agents such as anhydrides, especially acetic anhydride, or to use physical methods, such as distillation, for example, to remove leaving groups that are formed.

The molar ratio of anhydride to the compound of the formulae (XXXIa), (XXXIIa), (XXXIIIa), (XXXIVa) or (XXXVa) is in the range from 0.1:1 to 5:1, preferably in the range from 0.5:1 to 2:1.

Working up and isolation are carried out as described above.

A further embodiment of the process of the invention relates to preparing the benzofuran-2-ones (Ib) or (Ic) by reacting 3-oxobenzofuran-2-one (XXXVIa), or (XXXIa) and a compound of the formula (XXXVIb)

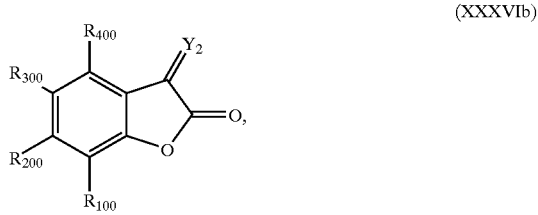

(XXXVIb)

with a compound of the formula (XXXVIIb)

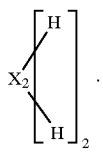

(XXXVIIb)

The reaction is normally started by contacting benzofuran-2-ones of the formula (XXXVIa), or (XXXVIa) and (XXXVIb), in analogy to known methods, with a compound of the formula (XXXVIIb), for example by mixing the starting components, or adding one starting product dropwise to the other, it being possible to react the benzofuran-2-ones (XXXVIa), or (XXXVIa) and (XXXVIb), in two portions or one portion.

In general, the molar ratio of a compound (XXXVIa), or (XXXVIa) and (XXXVIb), to a compound of the formulae (XXXVIIb) is in the range from 1:0.9 to 1:0.2; preferably, the molar ratio is situated within the range from 1:0.6 to 1:0.4.

If desired, the reaction may be conducted in an organic solvent or in a melt; preferably, the reaction is conducted in a solvent.

The chosen molar ratio of organic solvent to the compound (XXXVIa), or (XXXVIa) and (XXXVIb), is generally in the range from 500:1 to 1:2, preferably from 100:1 to 1:1.

The chosen reaction temperature is normally in the range from −20 to 250° C., preferably from 0 to 200° C.; preferably, the chosen reaction temperature is a temperature at which the reaction mixture boils and is situated in the range of the boiling temperature of the solvent used.

The pressure chosen is preferably atmospheric pressure.

The reaction time is normally chosen as a function of the reactivity of the starting products and of the chosen temperature, and is generally in the range from 10 minutes to 48 hours.

If desired, the reaction may be conducted in the presence of a catalyst.

In general, the chosen molar ratio of the catalysts to the compound of the formulae (XXXVIIb) is in the range from 0.001:1 to 5:1, preferably in the range from 0.001:1 to 1:1.

Both acidic and basic catalysts are suitable.

Catalysts, solvents, correspond to the definition given above.

Moreover, with particular preference the reaction is conducted in an inert gas atmosphere. Inert gases that can be used include noble gases, preferably helium and argon, and nitrogen.

It is found to be advantageous in the process of the invention to use additions of binding agents such as anhydrides, especially acetic anhydride, or to use physical methods, such as distillation, for example, to remove leaving groups that are formed.

The molar ratio of anhydride to the compound of the formula (XXXVIIb) is in the range from 0.1:1 to 5:1, preferably in the range from 0.5:1 to 2:1.

Working up and isolation are carried out as described above.

The starting compounds (XXXa), (XXXb), (XXXVIa) or (XXXVIb) are available commercially or are readily obtainable from phenols by reaction with glyoxal, for example, in accordance with the process of H.-D. Becker, K. Gustafsson, J. Org. Chem. 42, 2966 (1977).

The starting compounds of the formulae (XXXIa or b) may be prepared, for example, in analogy to processes from EP-B-632102 or Advanced Organic Chemistry, Jerry March, Ed. 1977, p. 824; those of the formulae (XXXIIa or b), for example, in analogy to processes from Advanced Organic Chemistry, Jerry March, Ed. 1977, p. 817, or Advanced Organic Chemistry, Jerry March, Ed. 1977, p. 824; those of the formulae (XXXIIIa or b), for example, in analogy to processes from U.S. Pat. No. 2,701,252; those of the formulae (XXXIVa or b), for example, in analogy to processes from Advanced Organic Chemistry, Jerry March, Ed. 1977, p. 810; or those of the formulae (XXXVa or b), for example, in analogy to processes from EP-B-632102; or those of the formulae (XXXVIIa or b), for example, in analogy to processes from DE-A1-19529262, or they are available commercially.

The 3-oxobenzofuran-2-ones can be prepared, for example, in analogy to known methods for the preparation of 3-unsubstituted furanone and 3-oxofuranone compounds. 3-Unsubstituted furanones, for example, may be prepared in analogy to the process of H.-D. Becker, K. Gustafsson, J. Org. Chem. 42, 2966 (1977) from phenols by reaction with glyoxal.

3-Oxobenzofuran-2-ones may be prepared, moreover, by oxidizing 3-unsubstituted benzofuran-2-ones, or by oxidizing 3-hydroxy-3-oxobenzofuran-2-ones in accordance with conventional methods for oxidizing hydroxy compounds to keto compounds. These methods are described, for example, in Houben-Weyl, Methoden der Organischen Chemie, 4th edition, volume 4/1a & 4/1b. In J. Org. Chem. 56, 6110 (1991), the oxidation with nitroxides is described by Z-Ma, J. M. Bobbitt. 3-Hydroxy-3-oxobenzofuran-2-ones may be prepared in analogy to the process which is described in U.S. Pat. No. 5,614,572. In addition, 3-oxobenzofuran-2-ones may be prepared in analogy to the process of D. J. Zwaneburg and W. A. P. Reyen which is described in Synthesis, 624, from 1976.

One particularly preferred embodiment of the present invention relates to the novel amino-hydroxy compounds of the formula (XLIa) or (XLIb)

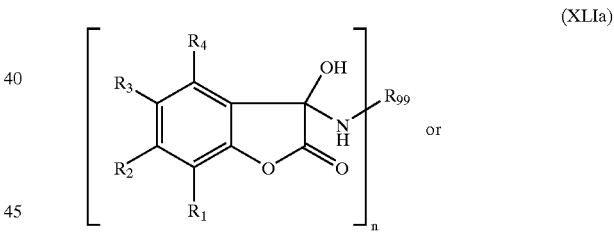

(XLIa)

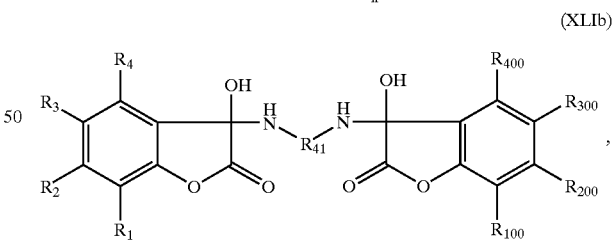

(XLIb)

in which
n is 1 or 2, and
if n is 1
$R_{99}$ is $R_{33}$, and
if n is 2
$R_{99}$ is $R_{41}$.

The present invention also provides a process for preparing amine-hydroxy compounds of the formulae (XLIa) or (XLIb) by reacting 3-oxobenzofuran-2-one (XXXVIa) with a compound of the formula (XXXVIIa)

H—X$_1$—H    (XXXVIIa), or reacting 3-oxobenzofuran-2-one (XXXVIa), or (XXXVIa) and (XXXVIb), with a compound of the formula (XXXVIIb)

Another particularly preferred embodiment of the present invention provides a process for preparing the compound of the formulae (XLIa) or (XLIb) by reacting 3-oxobenzofuran-2-one (XXXVIa) with a compound of the formula (XXXVIIa), or reacting 3-oxobenzofuran-2-one (XXXVIa), or (XXXVIa) and (XXXVIb), with a compound of the formula (XXXVIIb) in the presence of a catalyst, in particular a silicate catalyst.

Very particular preference is given, furthermore, to a process for preparing the compound of the formula (XLI) by reacting 3-oxobenzofuran-2-one (XXXVIa) with a compound of the formula (XXXVIIa) or reacting 3-oxobenzofuran-2-one (XXXVIa), or (XXXVIa) and (XXXVIb), with a compound of the formula (XXXVIIb) in the presence of a catalyst, particularly a silicate catalyst, at temperatures in the range from 0 to 200° C., preferably from 20 to 160° C., with particular preference from 20 to 40° C.

The present invention additionally provides a process for preparing the benzofuran-2-ones (Ia), (Ib) or (Ic) in which $X_1$ is a compound of the formula (IV) and $X_2$ is a compound of the formula (X), by coupling diazotized amines with coupling components in an aqueous medium, by reacting benzofuran-2-one (XXXa) or (XXXb) with a diazonium salt of the formula (XXXVIIIa).

 (XXXVIIIa)

or reacting benzofuran-2-one (XXXa), or (XXXa) and (XXXb), with a diazonium salt of the formula (XXXVIIIb)

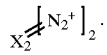 (XXXVIIIb)

The reaction is normally started by contacting the diazonium salt, commonly in the form of a solution, with benzofuran-2-one, for example by mixing the starting components or by adding one starting product dropwise to the other. The sequence of the addition is generally unimportant; preferably, benzofuran-2-one is added to a solution of the diazonium salt. Benzofuran-2-one may be in the form of a solution, dispersion or suspension; a solution is preferred.

For the preparation of the benzofuran-2-ones of the formula (Ia) the chosen molar ratio of a compound (XXXa) to a compound of the formula (XXXVIIIa) is generally in the range from 0.8:1 to 3:1; preferably, the molar ratio is situated within the range from 0.9:1 to 2:1.

For the preparation of the benzofuran-2-ones of the formulae (Ib) or (Ic) the chosen molar ratio of a compound (XXXa), or (XXXa) and (XXXb), to a compound of the formula (XXXVIIIb) is generally in the range from 1:0.9 to 1:0.2; preferably, the molar ratio is situated within the range from 1.0.66 to 1:0.4.

In general, the solvent chosen for the solution, dispersion or suspension is water, sodium acetate, sodium formate or an organic solvent such as formic, acetic, propionic acid, especially glycol ether such as ethylene glycol monoethyl ether or mixtures of these solvents, especially mixtures containing water.

The molar ratio of solvent to the compound (XXXa), or (XXXa) and (XXXb), is generally chosen in the range from 500:1 to 1:2, preferably from 100:1 to 1:1.

The reaction temperature is normally chosen in the range from −20 to 100° C., preferably from 0 to 50° C.

The pressure chosen is preferably atmospheric pressure.

The reaction time is commonly chosen as a function of the reactivity of the starting products and of the chosen temperature, and is generally situated within the range from 10 minutes to 48 hours.

If desired, the reaction may be conducted in the presence of nonionic, anionic or cationic surface-active substances which may have a cloud point in the aqueous medium. Where appropriate it is also possible to use further auxiliaries, such as natural synthetic resins or resin derivatives, or customary paint, printing ink or plastics additives.

The product may be isolated by the standard methods, such as by adding water and then carrying out filtration, or directly by filtration. The filter residue may be washed, if desired, with water, for example, and/or an organic solvent such as methanol, and then dried.

In one preferred embodiment of the process of the invention the crude product may, if desired, be heated to boiling in an organic solvent or recrystallized therefrom, and then isolated. For this purpose, in general, the crude product is admixed with an organic solvent and the resulting mixture is heated at boiling for from 1 to 24 hours. It is subsequently cooled, usually to a temperature in the range from −20 to 40° C., and the mixture is filtered, with the product being obtained as the filter residue. Normally thereafter the filter residue is dried in vacuo in the range from 40 to 200° C., preferably in the range from 60 to 120° C.

The starting products of the formulae (XXXVIIa) or (XXXVIIb) are readily accessible for example, in accordance with Houben Weyl 10/3.

The present invention likewise provides a process for preparing benzofuran-2-ones (Ia), (Ib) or (Ic) where $X_1$ is of the formula (V) and where $X_2$ is of the formula (XI) by formylation and subsequent reaction with an amine, by reacting benzofuran-2-one (XXXa) with a formylating reagent of the formula (XXXVIII)

$$R_{35}CO(OR_{36})_3 \quad\quad (XXXVIII)$$

and a compound of the formula (IXLa)

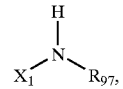 (IXLa)

in which $R_{97}$ possesses the same definition as $R_{32}$, or reacting benzofuran-2-one (XXXa), or (XXXa) and (XXXb), with a formylating reagent of the formula (XXXVIII) and a compound of the formula (IXLb)

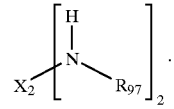 (IXLb)

The compounds of the formula (Ia), (Ib) or (Ic) are prepared in close analogy to a process described by O. S.

Wolfbeis and H. Junek in Z. Naturforsch, 34b, 283–289, 1979, by one-pot coupling reaction of three compounds, a methylene-active compound with a formylating reagent and an amine.

The further process parameters of the preparation correspond to those above for the preparation of the compound (Ia), (Ib) or (Ic) from benzofuran-2-one (XXXa) or (XXXa) and (XXXb) with a compound of the formula (XXXI a or b), (XXXII a or b), (XXXIII a or b), (XXXIV a or b), (XXXV a or b) or (XXXVII a or b).

Of course, many benzofuran-2-ones of the invention may alternatively be prepared from other benzofuran-2-ones of the invention by chemically modifying their substituents as functional groups without altering the benzofuran-2-one parent structure. The person skilled in the art knows countless methods with which substituents may be converted into other substituents, examples being those methods disclosed in the series "Compendium of Organic Synthetic Methods" (Wiley & Sons, New York, 1971 onwards). Owing to the known reactivity of benzofuran-2-one, appropriate reaction conditions are those under which it is not anticipated that its lactone bonds will be cleaved or its double bonds reduced. Depending on the nature of their substituents, the compounds of the formulae (Ia), (Ib) or (Ic) may be used to prepare novel benzofuran-2-ones of the formulae (Ia), (Ib) or (Ic). For example, novel ester or amide derivatives may be prepared in accordance with conventional synthesis methods for preparing esters or amides, as is described, for example, in Organic Syntheses, Collective Vol. I–VII. Preference is given in particular to esters prepared by transesterifying or esterifying compounds of the formula/formulae (Ia), (Ib) or (Ic) using, for example, various alcohols under conventional synthesis conditions and catalysis conditions, such as, for example, at temperatures from 0° C. to 200° C., with alcohol amounts of from 1 to 200 equivalents per equivalent of the compound of the formulae (Ia), (Ib) or (Ic), in the absence or presence of a solvent.

Dimeric benzofuran-2-ones are known in certain instances from WO 92/08703, as is their use as antioxidants.

The present invention further provides compositions comprising from 2 to 10, preferably 2 or 3, compounds of the formulae (Ia), (Ib) and/or (Ic) and/or (XLIa) and/or (XLIb) and/or dimeric benzofuran-2-ones of the formulae (XLIIa) and/or (XLIIb)

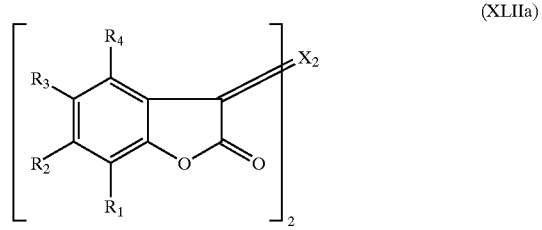

(XLIIa)

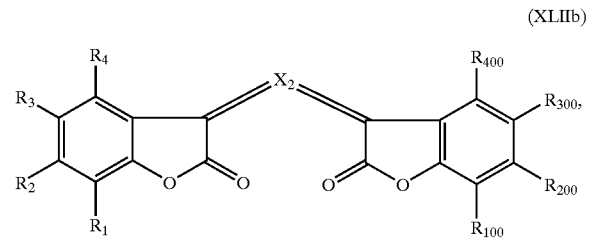

(XLIIb)

$X_2$ is $(C_6-C_{24})$arylene, $(A_5-A_{18})$heteroarylene or polymethylidene, polyether, polyimine, polyamine, or bi$(C_6-C_{24})$arylene or bi$(A_5-A_{18})$heteroarylene, which are connected to one another directly or via —C—, —N—, —O—, or a (—N═N—) unit.

The molar ratio of the composition comprising two compounds of the formulae (Ia), (Ib), (Ic), (XLIIa), (XLIIb), (XLIa) and/or (XLIb) is customarily in the range from 99:1 to 1:99.

The compositions comprising from 2 to 10 compounds may be prepared from the individual compounds by conventional methods of mixing.

One preferred embodiment of the present invention provides a process for preparing compositions by reacting from 2 to 10, with particular preference 2 or 3, different benzofuran-2-ones (XXXa) with a compound of the formulae (XXXIa), (XXXIIa), (XXXIIIa), (XXXIVa) or (XXXVa), or by reacting from 2 to 10, with particular preference 2 or 3, different 3-oxobenzofuran-2-ones (XXXVIa) with a compound of the formula (XXXVIIa).

The compounds of the formulae (Ia), (Ib), (Ic), (XLIIa), (XLIIb), (XLIa) or (XLIb) are appropriately used in an amount of from 0.01 to 70% by weight, usually from 0.01 to 30% by weight, preferably from 0.01 to 10% by weight, based on the high molecular mass organic material to be coloured.

In a further embodiment of the process of the invention it is also possible, if desired, to admix two or more compounds, preferably from 2 to 10 and with particular preference 2 or 3 compounds, of the formulae (Ia), (Ib), (Ic), (XLIIa), (XLIIb), (XLIa) or (XLIb) to the high molecular mass organic or inorganic material.

A further subject of the invention therefore constitutes a composition of matter comprising a high molecular mass organic material and at least one compound of the formulae (Ia), (Ib), (Ic), (XLIIa), (XLIIb), (XLIa) or (XLIb) or a composition comprising compounds of the formulae (Ia), (Ib), (Ic), (XLIIa), (XLIIb), (XLIa) or (XLIb) in a colouringly effective amount, generally in the range from 0.01 to 70% by weight, in particular from 0.01 to 30% by weight, preferably from 0.01 to 10% by weight, based on the high molecular mass organic material.

Furthermore, the present invention provides for the individual use of the compounds of the formulae (Ia), (Ib), (Ic), (XLIIa), (XLIIb), (XLIa) or (XLIb) as colorants, especially for colouring or pigmenting high or low molecular mass organic or inorganic material, especially the use of the compounds of the formulae (Ia), (Ib), (Ic), (XLIIa), (XLIIb), (XLIa) or (XLIb) and of the compositions of the invention, and also the compositions of matter, for preparing inks or colorants for paints, printing inks, mineral oils, lubricating greases or waxes, or dyed or pigmented plastics, non-impact-printing material, colour filters, cosmetics, toners.

It is, however, likewise possible to use the compositions of the invention comprising compounds of the formulae (Ia), (Ib), (Ic), (XLIIa), (XLIIb), (XLIa) or (XLIb). Compounds of the formulae (Ia), (Ib), (Ic), (XLIIa), (XLIIb), (XLIa) or (XLIb) may also be combined with colorants from a different chemical class, for example with dyes or pigments as selected, for example, from the group consisting of diketopyrrolopyrroles, quinacridones, perylenes, dioxazines, perinones, coumarins, anthraquinones, indanthrones, flavanthrones, indigos, thioindigos, quinophthalones, isoindolinones, isoindolines, phthalocyanines, metal complexes, azo pigments and azo dyes.

Depending on the nature of their substituents and of the polymer to be coloured, compounds of the formulae (Ia), (Ib), (Ic), (XLIIa), (XLIIb), (XLIa) or (XLIb) may be used as polymer-soluble dyes or as pigments. In the latter case it is advantageous to convert the as-synthesized products into a finely disperse form. This may be accomplished in a conventional manner. Depending on the compound and the intended use, it is found advantageous to use the colorants as toners or in the form of preparations.

The high molecular mass material may be organic or inorganic, and may comprise synthetic substances and/or natural substances. The substances in question may be, for example, natural resins or drying oils, rubber or casein, or modified natural substances such as chloro rubber, oil-modified alkyd resins, viscose, cellulose ethers or cellulose esters such as ethyl cellulose, cellulose acetate, propionate or butyrate, cellulose acetobutyrate, and nitrocellulose, but especially wholly synthetic organic polymers (thermosets and thermoplastics), as may be obtained by addition polymerization, for example by polycondensation or polyaddition. The class of the polymers includes, for example, polyolefins such as polyethylene, polypropylene, polyisobutylene, and also substituted polyolefins such as addition polymers of monomers such as vinyl chloride, vinyl acetate, styrene, acrylonitrile, acrylates, methacrylates, fluoro polymers such as polyfluoroethylene, polytrifluorochloroethylene or tetrafluoroethylenelhexafluoropropylene copolymer, and copolymers of the aforementioned monomers, especially ABS (acrylonitrile/butadiene/styrene) of EVA (ethylene/vinyl acetate). From the series of the polyaddition resins and polycondensation resins it is possible to use, for example, condensation products of formaldehyde with phenols, known as phenolic resins, and condensation products of formaldehyde and urea or thiourea, and also melamine, known as amino resins, and also the polyesters used as paint resins, either saturated ones such as alkyd resins or unsaturated ones such as maleic resins, and also linear polyesters, polyamides, polyurethanes, polycarbonates, polyphenylene oxides or silicones, silicone resins.

The abovementioned high molecular mass compounds may be present individually or in mixtures in the form of plastic masses, melts or spinning solutions. They may also be present in the form of their monomers or in the polymerized state in dissolved form as film formers or binders for paints or printing inks, such as, for example, linseed oil varnish, nitrocellulose, alkyd resins, melamine resins and urea-formaldehyde resins or acrylic resins.

The present invention therefore further provides for the use of the compositions of the invention comprising compounds of the formulae (Ia), (Ib), (Ic), (XLIIa), (XLIIb), (XLIa) or (XLIb) for preparing inks, for printing inks in printing processes, for flexographic printing, screen printing, packaging printing, security ink printing, gravure printing or offset printing, for pre-press stages and for textile printing, for office applications, domestic applications or graphics applications, such as for paper goods, for ballpoint pens, felt-tips, fibre-tips, card, wood, (wood)stains, metal, inking pads or inks for impact printing processes (with impact-pressure ink ribbons), for coating materials, for industrial or commercial use, for textile decoration and industrial marking, for roller coatings or powder coatings or for automotive finishes, for high-solids (low-solvent), waterborne or metallic coating materials or for pigmented formulations for aqueous paints, for mineral oils, lubricating greases or waxes, for the preparation of coloured plastics for coatings, fibres, sheets or mould carriers, for the preparation of non-impact-printing material for digital printing processes, for the thermal wax transfer printing process, the ink-jet printing process or for the thermal transfer printing process, and also for the preparation of polymeric ink particles, toners, dry copy toners, liquid copy toners or electrophotographic toners.

The present invention additionally provides inks comprising high molecular mass organic material and a colouringly effective amount of the compound of the formulae (Ia), (Ib), (Ic), (XLIIa), (XLIIb), (XLIa) or (XLIb) or the composition comprising compounds of the formulae (Ia), (Ib), (Ic), (XLIIa), (XLIIb), (XLIa) or (XLIb).

Processes for preparing inks, especially for ink-jet printing, are widely known and are described, for example, in U.S. Pat. No. 5,106,412.

The inks may be prepared, for example, by mixing the compounds of the invention with polymeric dispersants.

The mixing of the compounds of the invention with the polymeric dispersant takes place preferably in accordance with conventional methods of mixing, such as stirring or mechanical mixing; preferably it is advisable to use intensive mixers such as an Ultra-Turrax.

When mixing the compounds of the invention with polymeric dispersants it is appropriate to use a water-dilutable organic solvent.

The weight ratio of the compounds of the invention to the ink is appropriately chosen in the range from 0.0001 to 75% by weight, preferably from 0.001 to 50% by weight, based on the overall weight of the ink.

The present invention therefore also provides a process for preparing inks by mixing with one another high molecular mass organic material and a colouringly effective amount of the compounds of the formulae (Ia), (Ib), (Ic), (XLIIa), (XLIIb), (XLIa) or (XLIb) or the compositions comprising compounds of the formulae (Ia), (Ib), (Ic), (XLIIa), (XLIIb), (XLIa) or (XLIb).

The present invention additionally provides colorants comprising high molecular mass organic material and a compound of the formula (I) and/or (XLI) of the invention and/or compounds of the formula (XLII) or a composition of the invention, in a colouringly effective amount.

Moreover, the present invention provides a process for preparing colorants by mixing a high molecular mass organic material and a colouringly effective amount of the compounds of the formulae (Ia), (Ib), (Ic), (XLIIa), (XLIIb), (XLIa) or (XLIb) of the invention or composition of the invention comprising compounds of the formulae (Ia), (Ib), (Ic), (XLIIa), (XLIIb), (XLIa) or (XLIb).

In addition, the present invention provides coloured plastics or polymeric ink particles comprising high molecular mass organic material and compounds of the formulae (Ia), (Ib), (Ic), (XLIIa), (XLIIb), (XLIa) or (XLIb), or composition comprising compounds of the formulae (Ia), (Ib), (Ic), (XLIIa), (XLIIb), (XLIa) or (XLIb), in a colouringly effective amount.

Furthermore, the present invention provides a process for preparing coloured plastics or polymeric ink particles by mixing with one another a high molecular mass organic material and a colouringly effective amount of the compounds of the formulae (Ia), (Ib), (Ic), (XLIIa), (XLIIb), (XLIa) or (XLIb), or composition comprising compounds of the formulae (Ia), (Ib), (Ic), (XLIIa), (XLIIb), (XLIa) or (XLIb).

The colouring of the high molecular mass organic substances with the colorants of the compounds of the formulae (Ia), (Ib), (Ic), (XLIIa), (XLIIb), (XLIa) or (XLIb), or with the compositions comprising compounds of the formulae (Ia), (Ib), (Ic), (XLIIa), (XLIIb), (XLIa) or (XLIb), takes place, for example, by mixing such a colorant, in the form, where appropriate, of masterbatches, into these substrates using roll mills, mixing or grinding apparatus to dissolve or finely disperse the colorant in the high molecular mass material. The high molecular mass organic material with the admixed colorant is subsequently processed by methods known per se, such as by calendering, compression, extrusion, coating, spinning, casting or injection moulding, whereby the coloured material acquires its ultimate shape. The admixing of the colorant may also be carried out directly prior to the actual processing step, for example by continuously metering in a pulverulent colorant of the invention and a granulated, high molecular mass organic material, and also, if desired, additional substances such as additives, simultaneously and directly into the inlet zone of an extruder, where the mixing-in takes place just prior to processing. In general, however, prior mixing of the colorant into the high molecular mass organic material is preferable, since more uniform results may be obtained.

It is frequently desired to incorporate plasticizers into the high molecular mass compounds, prior to shaping, in order to produce non-rigid mouldings or to reduce their brittleness. Examples of useful plasticizers are esters of phosphoric acid, phthalic acid or sebacic acid. In the process of the invention, the plasticizers may be incorporated into the polymers before or after the colorant has been incorporated. It is also possible, for the purpose of achieving different hues, to add to the high molecular mass organic materials not only the compounds of the formulae (Ia), (Ib), (Ic), (XLIIa), (XLIIb), (XLIa) or (XLIb), or the compositions of the invention, but also constituents such as white, chromatic or black pigments in any desired amounts.

To colour paints and printing inks, the high molecular mass organic materials and the compounds of the formulae (Ia), (Ib), (Ic), (XLIIa), (XLIIb), (XLIa) or (XLIb), or compositions of the invention, together if desired with additives such as fillers, dyes, pigments, siccatives or plasticizers, are finely dispersed or dissolved in a common organic solvent or solvent mixture. This may be accomplished by dispersing or dissolving the individual components by themselves, or else two or more together, and only then combining all of the components. Processing is effected by customary methods, for example by spraying, film-drawing or one of the many printing methods, after which the paint or printing ink, after drying beforehand if desired, is subjected appropriately to thermal or radiative curing.

Where the high molecular mass material to be coloured is a paint, it may be a standard paint or else a speciality paint, for example an automotive paint, preferably a metallic effect coating comprising, for example, metal particles or mica particles.

Preference is given to the coloration of thermoplastics, including in particular those in the form of fibres, and of printing inks. Preferred high molecular mass organic materials which may be coloured in accordance with the invention are, very generally, polymers having a dielectric constant $\geq 2.5$, especially polyesters, polycarbonate (PC), polystyrene (PS), polymethyl methacrylate (PMMA), polyamide, polyethylene, polypropylene, styrene/acrylonitrile (SAN) or acrylonitrile/butadiene/styrene (ABS). Particular preference is given to polyesters, polycarbonate, polystyrene and PMMA. Very particular preference is given to polyesters, polycarbonate or PMMA, especially aromatic polyesters which may be obtained by polycondensation of terephthalic acid, such as polyethylene terephthalate (PET) or polybutylene terephthalate (PBTP), for example.

Particular preference is also given to the colouring of low molecular mass organic material such as mineral oils, lubricating greases and waxes using the compounds of the invention.

Moreover, the present invention provides non-impact-printing material comprising high molecular mass organic material and a compound of the formulae (Ia), (Ib), (Ic), (XLIIa), (XLIIb), (XLIa) or (XLIb), or composition comprising compounds of the formulae (Ia), (Ib), (Ic), (XLIIa), (XLIIb), (XLIa) or (XLIb), in a colouringly effective amount.

Moreover, the present invention provides a process for preparing non-impact-printing material by mixing with one another a high molecular mass organic material and a colouringly effective amount of the compounds of the formulae (Ia), (Ib), (Ic), (XLIIa), (XLIIb), (XLIa) or (XLIb), or composition comprising compounds of the formulae (Ia), (Ib), (Ic), (XLIIa), (XLIIb), (XLIa) or (XLIb).

Moreover, the present invention provides toners comprising high molecular mass organic material and a compound of the formulae (Ia), (Ib), (Ic), (XLIIa), (XLIIb), (XLIa) or (XLIb), or composition comprising compounds of the formulae (Ia), (Ib), (Ic), (XLIIa), (XLIIb), (XLIa) or (XLIb), in a colouringly effective amount.

Moreover, the present invention provides a process for preparing toners by mixing with one another a high molecular mass organic material and a colouringly effective amount of the compounds of the formulae (Ia), (Ib), (Ic), (XLIIa), (XLIIb), (XLIa) or (XLIb), or composition comprising compounds of the formulae (Ia), (Ib), (Ic), (XLIIa), (XLIIb), (XLIa) or (XLIb).

In one particular embodiment of the process of the invention, toners, paints, inks or coloured plastics are prepared by processing masterbatches of toners, paints, inks or coloured plastics in roll mills or mixing or grinding apparatus.

In the present invention, a colouringly effective amount of the compounds of the formulae (Ia), (Ib), (Ic), (XLIIa), (XLIIb), (XLIa) or (XLIb), or composition comprising compounds of the formulae (Ia), (Ib), (Ic), (XLIIa), (XLIIb), (XLIa) or (XLIb), is generally from 0.0001 to 99.99% by weight, preferably from 0.001 to 50% by weight and with particular preference from 0.01 to 50% by weight, based on the overall weight of the material coloured or pigmented therewith.

When the compounds of the formulae (Ia), (Ib), (Ic), (XLIIa), (XLIIb), (XLIa) or (XLIb), or the compositions of the invention, are present in solution in the polymers employed, they are notable for a clean hue, high colour strength, good light, heat and weathering fastness, especially in PET, PMMA, PS and PC, and, furthermore, for a high level of fluorescence. The colorations obtained, for example, in thermoplastics or thermosets, fibres, paints or printing inks are notable for a clean hue, high colour strength, high saturation, high transparency, good fastness to overcoating, migration, rubbing, light, weathering and especially heat, and for good gloss. The colorants possess good dispersibility and generally good solubilities in organic solvents. In mixtures comprising the compounds of the invention, beautiful colour shades are obtained.

The compositions of the invention may exhibit advantages in terms of applicational properties over individual compounds.

The examples which follow illustrate the invention without in any way restricting it:

The preparations of 5,7-di-tert-butyl-3H-benzofuran-2-one, 5-methoxy-7-tert-butyl-3H-benzofuran-2-one and methyl 3-tert-butyl-3H-benzofuran-2-one-5-yl)propionate take place in analogy to H.-D. Becker, K. Gustafsson: J. Org. Chem. 42, 2966 (1977).

EXAMPLE 1a

A 15 l multi-necked vessel with stirrer, dropping funnel, water separator, condenser and thermometer is charged with stirring and in succession with 300 ml of toluene, 212 g of 97% 2,4-di-tert-butylphenol (Aldrich 99%), 121.9 ml of 50% strength aqueous glyoxylic acid and 0.5 g of p-toluenesulfonic acid monohydrate. The reaction mixture is subsequently refluxed vigorously with thorough stirring. This is accompanied by the separation of the water present in the glyoxylic acid, and the water of reaction from the first stage. After a reflux time of about 3 h, the separation of water ends, to leave a homogeneous, pale yellow solution of 5,7-di-t-butyl-3-hydroxybenzofuran-2-one. Thereafter, the toluene is distilled off under atmospheric pressure and with a heating-bath temperature of up to 142° C. The crystalline solid is subsequently dried at 80° C./50 mbar.

EXAMPLE 1b 30 g (114 mmol) of 5,7-di-tert-butyl-3-hydroxybenzofuran-2-one, prepared in accordance with Example 1a, is dissolved in 200 ml of dimethyl sulfoxide. 54 ml (574 mmol) of acetic anhydride is added to the solution over 2 minutes with vigorous stirring, and stirring is continued for 15 hours at from 25 to 27° C. With stirring, the reaction mixture is poured into 2 litres of water and stirred for 2 hours. The precipitate is filtered off with suction and washed with 1 litre of water, then conc. sodium chloride solution (25% by weight) and then with 1 litre of water. The precipitate is subsequently dried at 80° C./15 mbar. This gives 31.10 g of orange crystals of 5,7-di-tert-butyl-3-oxobenzofuran-2-one.

EXAMPLE 1c

A solution of 5,7-di-tert-butyl-3-oxobenzofuran-2-one, 4 g (15.4 mmol), prepared in accordance with Example 1b, and ethyl 1,2-dihydro-4-(4-chlorophenyl)pyrrolone-3-carboxylate, 4.46 g (obtainable in accordance with Bull. Soc. Chem. Belg., 97, 8–9, 615, 1988) in 100 ml of acetic acid is boiled under reflux for 17 h. Thereafter the solvent is distilled off at 60° C./60 mbar and the product is chromatographed on silica gel (0.02–0.064 mm) using 3 litres of toluene. This gives 2.96 g of reddish brown powder of a compound of the formula (XLIII)

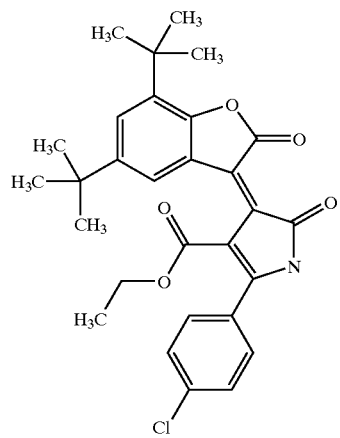

(XLIII)

EXAMPLE 2

5,7-Di-tert-butyl-3-oxobenzofuran-2-one, 4 g (15.4 mmol), prepared as in Example 1b, is dissolved together with barbituric acid, 2.14 g, (Fluka) in 100 ml of acetic acid and the solution is boiled under reflux for 17 hours. The solvent is subsequently distilled off with 60 mbar/60° C. and then 250 ml of methanol are added to the residue. A bright yellow product is precipitated which is filtered off with suction and dried in vacuo at 50 mbar/40° C. This gives 0.17 g of a compound of the formula (XLIV)

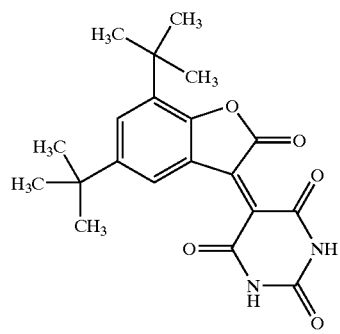

(XLIV)

EXAMPLE 3

5,7-Di-t-butyl-3-oxobenzofuran-2-one, 4 g (15.4 mmol), prepared in accordance with Example 1b, and 2-methoxy-4-nitroaniline, 2.56 g (15.4 mmol) (Fluka), are dissolved in 100 ml of toluene. 50 mg of para-toluenesulfonic acid (Fluka) are added as catalyst to this solution, which is then boiled under reflux for 6 hours. The solvent is subsequently evaporated off under 60° C./75 mbar vacuum and the residue is recrystallized from 100 ml of methanol. This gives 2.08 g of dark yellow crystals of the formula (XLV)

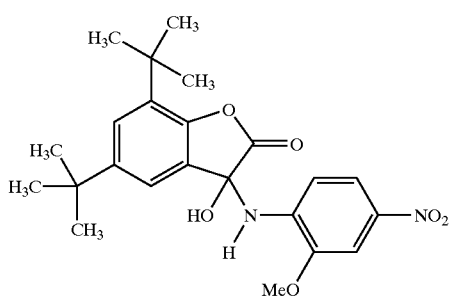

(XLV)

EXAMPLE 4–6

5,7-Di-tert-butyl-3-oxobenzofuran-2-one, 4 g (15.4 mmol), prepared in accordance with Example 1b, and 2-methoxy-4-nitroaniline, 2.56 g (15.4 mmol) (Fluka), are dissolved in 100 ml of cyclohexane. 4 g of a silicate are added as catalyst (see Table 1) to this solution, which is subsequently stirred at from 25 to 27° C. for 24 h. The solvent is then evaporated off at 60° C. under 100 mbar vacuum and the residue is washed with 100 ml of methanol and dried in vacuo (50 mbar) at 27° C. This gives 2.08 g of dark yellow crystals of the formula (IL).

TABLE 1

| Catalyst | Yield | Example |
| --- | --- | --- |
| Fulkat 40 from Pontecchio Marconi | 3.89 g | 4 |
| Katalysator K10 from Süd-Chemie | 3.88 g | 5 |
| Katalysator Rudex from Rudex Nebelova Bratislava | 3.57 g | 6 |

Table 2:

Preparation as for Examples 4–6 but with the difference that, instead of the 2-methoxy-4-nitroaniline, use is made in Example 7, of 5-aminobenzimidazolone (Clariant), 2.29 g (15.4 mmol), in Example 8, of 2,4-methoxyaniline, 2.36 g (15.4 mmol), under the same conditions, and in Example 9, of 3-nitroaniline, 2.21 g (15.4 mmol), using xylene as solvent at 140° C. Silicate K10 is used as catalyst for Examples 7–9.

| Product | Yield | Example |
| --- | --- | --- |
| (XLVI) | 1.41 g pale yellow powder | 7 |
| (XLVII) | 2.82 g orange crystals. | 8 |
| (XLVIII) | 1.82 g yellow crystals | 9 |

EXAMPLE 10

5,7-Di-t-butyl-3-oxobenzofuran-2-one, 4 g (15.4 mmol), prepared in accordance with Example 1b, and 2,2'-dichlorobenzidine, 1.92 g, are dissolved in 100 ml of ethanol and the solution is boiled under reflux at 76° C. for 13 hours. The solvent is then evaporated off at 50° C./1175 mbar and the residue is washed with 100 ml of methanol and dried under 50 mbar at 27° C. This gives 0.58 g of yellow crystals of the formula (L)

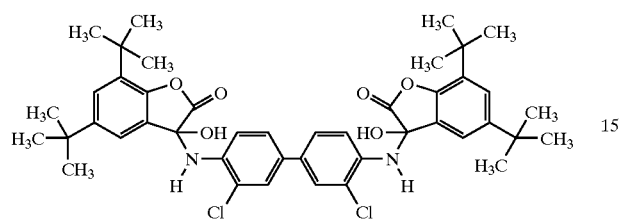

(L)

EXAMPLE 11

5,7-Di-tert-butyl-3H-benzofuran-2-one, 4.93 g, prepared as in Example 1a and dissolved in 20 ml of toluene, is added to a suspension of sodium hydride, 0.88 g (*Fluka pract.*) in 20 ml of toluene. Subsequently, benzophenone (*Fluka purum*), 3.46 g, is added. The resulting mixture is heated to boiling and stirred at boiling temperature for 15 hours. The mixture is then admixed with acetic acid (*Fluka puriss.*), 1.32 g, then cooled to room temperature and extracted with 50 ml of toluene. The organic phase is dried over $Na_2SO_4$ and concentrated and the residue is crystallized from methanol. The crystals are filtered off and the filter residue is dried in a drying oven at 60° C. This gives 2.5 g of a yellow powder of the formula (LI)

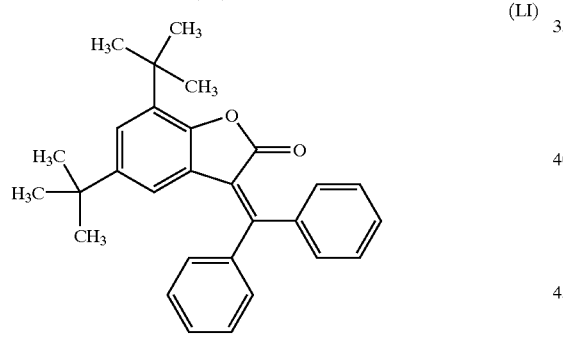

(LI)

EXAMPLE 12

In a manner very similar to that for the preparation of Example 11, from 4,4'-bisdimethyl-aminobenzophenone (*Fluka purum*), 1.2 g of an orange compound of the formula (LII) are obtained

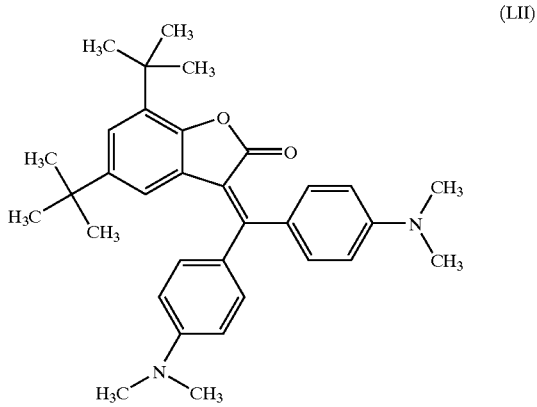

(LII)

EXAMPLE 13

To a boiling solution of 5,7-di-tert-butyl-3H-benzofuran-2-one, 1.5 g, in 50 ml of acetic acid is added, 2-cyano-N-(3,4-dichlorophenyl)-2-(3-imino-2,3-dihydro-1H-isoindol-1-yl)acetamide, 2.43 g, prepared in accordance with EP 657507 A2. The mixture is stirred further under reflux for 19 hours, then cooled to room temperature and the orange suspension formed is subsequently filtered. The filter residue is washed with acetic acid and then with water. The moist filter residue is dried in a vacuum drying oven at 80° C. This gives 2.74 g of an orange powder of the formula (LIII), which when incorporated into PET gives an orange colour.

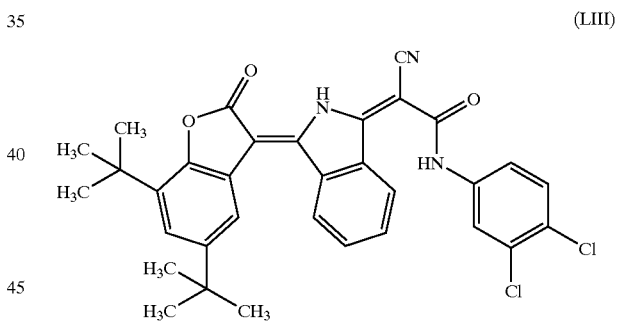

(LIII)

EXAMPLE 14–17

In analogy to the process in Example 13, the compounds of Table 3 are prepared:

TABLE 3

|  | Colour | Example |
|---|---|---|
| (LIV) with $x_7 = 4\text{-}Cl$ | orange | 14a |

TABLE 3-continued

|  | | Colour | Example |
|---|---|---|---|
| see above | (LIV) with $x_8$ = 2-COOCH$_3$ | orange | 14b |
| 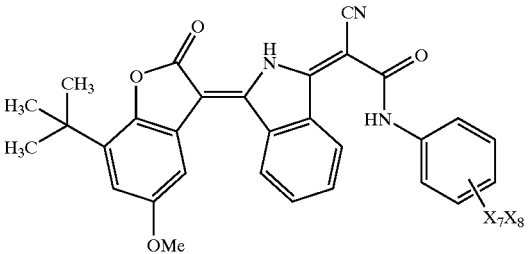 | (LV) with $x_7$ = 4-Cl | dark red | 14a |
| see above | (LVI) with $x_7x_8$ = 3,4-bis-Cl | dark red | 15b |
| see above | (LVII) with $x_7$ = 2-COOCH$_3$ | dark red | 15c |
| 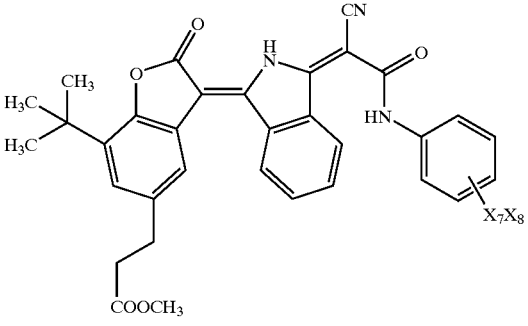 | (LVIII) with $x_7$ = 4-Cl | red | 16a |
| see above | (LIX) with $x_7,x_8$ = 3,4-bis-Cl | red | 16b |
| see above | (LX) with $x_7$ — 2-COOCH$_3$ | red | 16c |
| 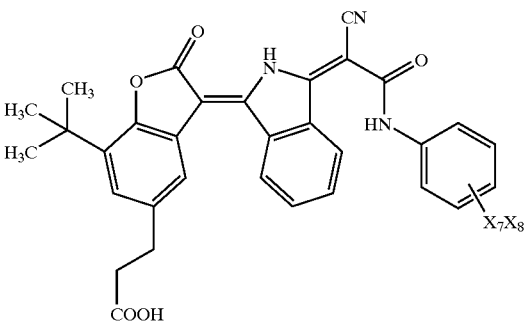 | (LXI) with $x_7$ = 4-Cl | red | 17a |
| see above | (LXII) with $x_7x_8$ = 3,4-bis-Cl | red | 17b |
| see above | (LXIII) with $x_7$ = 2-COOCH$_3$ | red | 17c |

*7.4 g of the compound of the formula (LVIII), (LIX) or (LX) are heated at reflux in 300 ml of acetic acid with 3 ml of methanesulfonic acid for 56 hours. Then 100 ml of acetic acid are distilled off and the residue is poured into 1200 ml of water. The red precipitate is filtered off, washed with water and dried. This gives the compound of the formula (LXI), (LXII) or (LXIII).

EXAMPLE 18

2.3 g of 1-aminoanthraquinone and 2.2 ml of trimethyl orthoformate (*Fluka purum*) in 10 ml of acetic acid are added to 2.46 g of 5,7-di-tert-butyl-3H-benzofuran-2-one in 10 ml of acetic acid solution. The mixture is stirred at 105° C. for 2.5 hours. After cooling to room temperature, the mixture is filtered. The filter residue is washed with acetic acid and then with water and then dried in a drying oven at 60° C. and 200 mbar. This gives 3.7 g of a violet powder of the formula (LXIV)

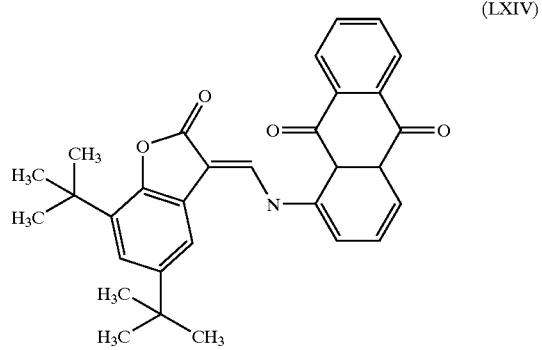

(LXIV)

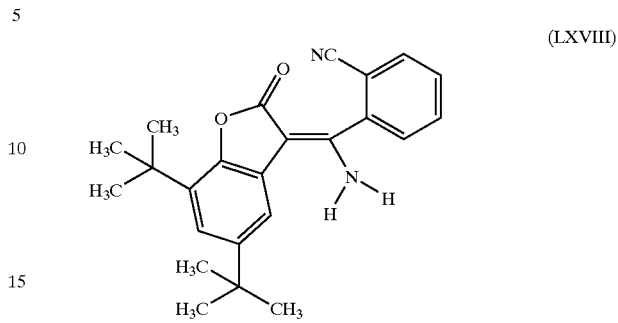

(LXVIII)

The filter residue is purified by column chromatography (Merck silica gel, eluent: hexane/ethyl acetate 4:1 to 1:4) and dried in a drying oven at 60° C. and 200 mbar. This gives 3.1 g of a red powder of the formula (LXVIII)

EXAMPLE 19–21

In analogy to the process in Example 18, the compounds of Table 4 are prepared:

EXAMPLE 23

5-Aminobenzimidazolone (1.49 g, Aldrich) is dissolved at 40° C. in 70 ml of water and 11 ml of acetic acid, and 2.7 ml of 32% hydrochloric acid are added. The solution is subsequently cooled to 5° C. Following the dropwise addition of 2.75 ml of 4N $NaNO_2$ solution and 0.5 hour of stirring at 5° C., the solution is filtered and then the excess nitrite is decomposed using sulfamic acid. Subsequently, 6 g of sodium acetate dissolved in 5 ml of acetic acid are added. 5,7-Di-t-butyl-3H-benzofuran-2-one, 2.34 g, dissolved in 35 ml of ethylcellosolve is added dropwise at 5° C. to the

TABLE 4

| | | Example | Colour |
|---|---|---|---|
| (LXV) | ![structure] | 19 | yellow |
| (LXVI) | ![structure] | 20 | dark red |
| (LXVII) | ![structure] | 21 | yellow |

EXAMPLE 22

A mixture of potassium carbonate, 1.78 g, phthalodinitrile, 1.5 g, and 4.7 ml of 7N ammonia solution in 30 ml of methanol is stirred at reflux for 12 hours. Thereafter, the resulting mixture is cooled to room temperature, and 5,7-di-t-butyl-3H-benzofuran-2-one, 2.88 g, in 4.7 ml of acetic acid is added. The mixture is stirred at reflux for 4 hours and then cooled and subsequently filtered.

resulting mixture, which is then stirred at room temperature for 3 hours and subsequently at 50° C. for 2 h. Thereafter, the mixture obtained is filtered at 50° C. and the filter residue is washed with water and subsequently dried at 80° in a vacuum drying oven. 3.3 g of a yellow powder (LIXX) are isolated, which when incorporated in PVC gives a yellow coloration.

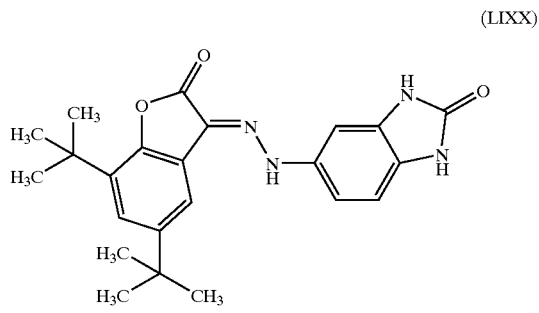

(LIXX)

EXAMPLE 24

A suspension of dichlorobenzidine (*Fluka purum*), 2.53 g, in 27 ml of acetic acid and 3.4 ml of concentrated hydrochloric acid (32%) and 150 g of ice-water is admixed dropwise with 2.5 ml of 4N sodium nitrite solution at 0–5° C. and subsequently stirred at this temperature for 45 minutes. The resulting brown suspension is admixed dropwise at 10° C. over the course of 1 hour with a solution of 4.93 g of 5,7-di-t-butyl-3H-benzofuran-2-one in 70 ml of ethylcellosolve, 5 ml of acetic acid and 10 ml of saturated sodium acetate solution and is subsequently stirred at room temperature for 10 hours. The suspension obtained is filtered and the filter residue is washed with water. Subsequently, 50 ml of acetic acid are added to the filter residue, which is then heated under reflux for 2 hours. The mixture obtained is then filtered again and, subsequently, the filter residue is washed with water and dried in a vacuum drying oven at 80° C. This gives 2.15 g of a yellow-brown powder of the formula (LXX), which when incorporated into PVC gives a yellow colour.

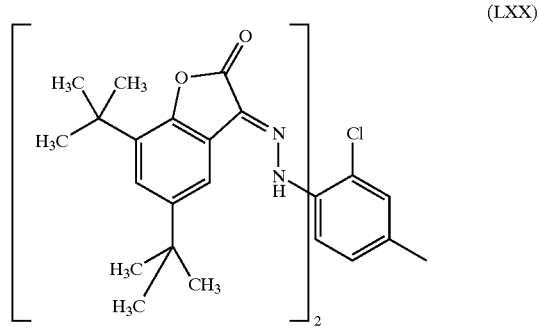

(LXX)

EXAMPLE 25

A suspension of 5.75 g of aminoanthraquinone (*Fluka purum*) in 90 ml of acetic acid and 7.5 ml of concentrated hydrochloric acid (32%) is admixed dropwise at 0–5° C. with 6.25 ml of 4N sodium nitrite solution and then stirred at this temperature for 70 minutes. To the resulting mixture is added a solution of 6.16 g of 5,7-di-t-butyl-3H-benzofuran-2-one in 40 ml of 2-ethoxyethanol (Merck) at 5° C., followed by 30 g of sodium acetate, after which the mixture is stirred at room temperature for 3 h. The orange suspension obtained is diluted with 250 ml of water and filtered and the filter residue is washed with water and methanol. The filter residue is dried in a vacuum drying oven at 80° C. This gives 10.2 g of an orange powder of the formula (LXXI), which when incorporated into PET gives an orange colour.

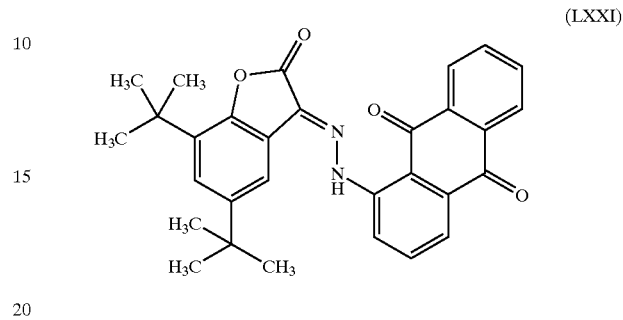

(LXXI)

EXAMPLE 26

Process analogous to Example 25, but differing in that aminoanthraquinone is replaced with 2,5-dichloroaniline (*Fluka purum*). This gives 0.35 g of a yellow powder of the formula (LXXII), which when incorporated into PVC gives a yellow colour.

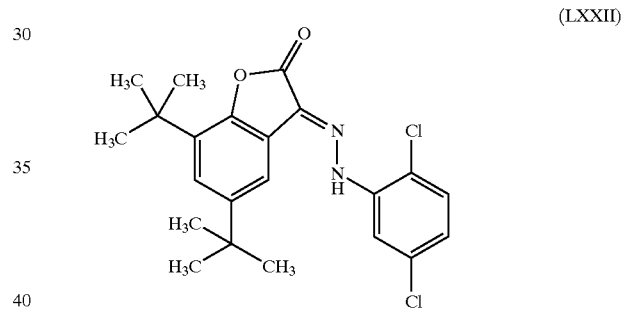

(LXXII)

EXAMPLE 26

Process analogous to Example 25, but differing in that aminoanthraquinone is replaced with 2-nitro-4-methoxyaniline (*Fluka purum*). This gives 5.7 g of an orange powder of the formula (LXXIII), which when incorporated into PVC gives a yellow colour.

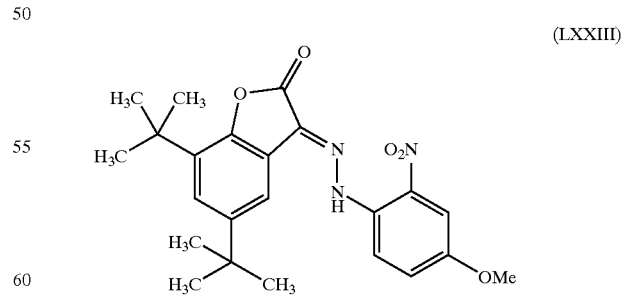

(LXXIII)

EXAMPLE 27

15 g of vinyl copolymer (with 13% acetate, 86% chlorine and 1% copolymerized maleic acid, e.g. VINYLITE VMCH from UCC) is stirred into 30 g of toluene and 50 g of methyl ethyl ketone and brought into solution completely (dissolver for about 20 minutes or propeller stirrer for about 1 hour). Subsequently, 5 g of a lactone dye of the formulae (XLIII-LXXIII) are incorporated by stirring for 5–15 minutes. The printing ink prepared in this way is applied to aluminium or to metallized polymer films or used as the basis for a hot stamp onto a polyester film.

EXAMPLE 28

Preparation of Injection-Moulded Plaques in Polyethylene Terephthalate (PET)

0.3 g of compound of the formulae (XLIII-LXXIII) is mixed with 1500 g of polyethylene terephthalate (PET) (™MELINAR PURA, ICI), predried at 120° C. briefly by hand, then on a tumble mixer at 50 rpm for 5 min. This mixture is subsequently preextruded at 270° C. on a 25 mm single-screw extruder (Collin).

The compound is subsequently processed on a microprocessor-controlled injection moulding machine (™Ferromatik FM 40, Klöckner). The residence time of the polymer (dependent on cycle time, screw volume and plastification volume) is 5 min, during which backpressure and screw speed are kept low. This is beneficial to the homogeneity of the plastic and prevents the generation of frictional heat. The first mouldings (plaques 65×25×1.5 mm in size) are discarded.

The moulding obtained at 270° C., 280° C., 290° C. and 300° C. are notable for very high heat stability, high light fastness, good migration resistance and high colour strength.

What is claimed is:

1. A compound of the formula (Ia), (Ib) or (Ic)

$$Q_1=X_1 \quad \text{(Ia)}$$

$$Q_1=X_2=Q_1 \quad \text{(Ib)}$$

$$Q_2=X_2=Q_2 \quad \text{(Ic)}$$

in which $Q_1$ is a benzofuran-2-one of the formula (IIa), and $Q_2$ is a benzofuran-2-one of the formula (IIb)

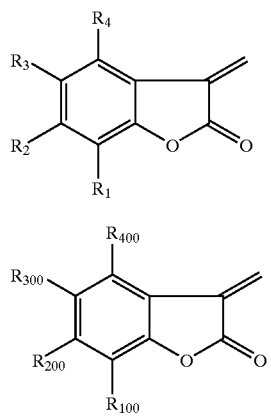

(IIa)

(IIb)

in which $R_1, R_2, R_3, R_4, R_{100}, R_{200}, R_{300}$ or $R_{400}$ independently of one another are hydrogen, halogen, hydroxyl, cyano, ether, nitro, an amine, amide, imine, urethane, sulfonamide, ester, carboxylic acid or sulfonic acid radical or carboxylic salt, sulfonic salt or $C_1$–$C_{24}$alkyl, $C_1$–$C_{24}$alkoxy, $C_1$–$C_{24}$alkylthio, $C_5$–$C_{12}$cycloalkyl, $C_5$–$C_{12}$cycloalkoxy, $C_5$–$C_{12}$cycloalkylthio, $C_2$–$C_{24}$alkenyl, $C_6$–$C_{24}$aryl, $C_7$–$C_{25}$aralkyl, $C_6$–$C_{24}$aryloxy, $C_6$–$C_{24}$arylthio, thienyl, benzo[b,d]thienyl, dibenzo[b,d]thienyl, thianthrenyl, furyl, furfuryl, 2H-pyranyl, benzofuranyl, isobenzofuranyl, benzimidazolyl, benzothiazolyl, dibenzofuranyl, phenoxythiinyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, O-thienyl, O-benzo[b]thienyl, O-dibenzo[b,d]thienyl, O-thianthrenyl, O-furyl, O-furfuryl, O-2H-pyranyl, O-benzofuranyl, O-isobenzofuranyl, O-benzimidazolyl, O-benzothiazolyl, O-dibenzofuranyl, O-phenoxythiinyl, O-pyrrolyl, O-imidazolyl, O-pyrazolyl, O-pyridyl, O-bipyridyl, O-triazinyl, O-pyrimidinyl, O-pyrazinyl, b-pyridazinyl, O-indolizinyl, O-isoindolyl, O-indolyl, O-indazolyl, O-purinyl, O-quinolizinyl, O-quinolyl, O-isoquinolyl, O-phthalazinyl, O-naphthyridinyl, O-quinoxalinyl, O-quinazolinyl, O-cinnolinyl, O-pteridinyl, O-carbazolyl, O-carbolinyl, O-benzotriazolyl, O-benzoxazolyl, O-phenanthridinyl, O-acridinyl, O-perimidinyl, O-phenanthrolinyl, O-phenazinyl, O-isothiazolyl, O-phenothiazinyl, O-isoxazolyl, O-furazanyl or O-phenoxazinyl, S-thienyl, S-benzo[b]thienyl, S-dibenzo[b,d]thienyl, S-thianthrenyl, S-furyl, S-furfuryl, S-2H-pyranyl, S-benzofuranyl, S-isobenzofuranyl, S-benzimidazolyl, S-benzothiazolyl, S-dibenzofuranyl, S-phenoxythiinyl, S-pyrrolyl, S-imidazolyl, S-pyrazolyl, S-pyridyl, S-bipyridyl, S-triazinyl, S-pyrimidinyl, S-pyrazinyl, S-pyridazinyl, S-Indolizinyl, S-isoindolyl, S-indolyl, S-indazolyl, S-purinyl, S-quinolizinyl, S-quinolyl, S-isoquinolyl, S-phthalazinyl, S-naphthyridinyl, S-quinoxalinyl, S-quinazolinyl, S-cinnolinyl, S-pteridinyl, S-carbazolyl, S-carbolinyl, S-benzotriazolyl, S-benzoxazolyl, S-phenanthridinyl, S-acridinyl, S-perimidinyl, S-phenanthrolinyl, S-phenazinyl, S-isothiazolyl, S-phenothiazinyl, S-isoxazolyl, S-furazanyl or S-phenoxazinyl, or $R_1$ and $R_2$, $R_2$ and $R_3$, $R_3$ and $R_4$ or $R_{100}$ and $R_{200}$, or $R_{200}$ and $R_{300}$, $R_{300}$ and $R_{400}$, independently of one another in each case together are divalent radicals selected from the group consisting of polycyclic radicals, 1,3-butadien-1,4-ylene and —CH=CH—NH—, the two last radicals forming an additional fused-on 5- or 6-membered ring, and $X_1$ is a hydrazone or imine radical, with the proviso that, if $R_1, R_2, R_3$ and $R_4$ are hydrogen, or at least one $R_1, R_2, R_3$ or $R_4$ is methyl, the hydrazone radical is excluded, or, if $R_1, R_2, R_3$ or $R_4$ is hydrogen, $X_1$ is not phenylimine- or 4-dimethylamine-phenylimine, or $X_1$ is a methylene radical,

in which $Q_3$ is a primary or secondary amine radical and $Q_4$ is hydrogen or $C_1$–$C_{24}$alkyl, —CO—($C_1$–$C_{24}$alkyl), —CO—O—($C_1$–$C_{24}$alkyl), $C_1$–$C_{24}$alkoxy, $C_1$–$C_{24}$alkylthio, $C_5$–$C_{12}$cycloalkyl, $C_5$–$C_{12}$cycloalkoxy, $C_5$–$C_{12}$cycloalkylthio, $C_2$–$C_{24}$alkenyl, $C_6$–$C_{24}$aryl, —CO—O—($C_6$–$C_{24}$aryl), —CO—($C_6$–$C_{24}$aryl), $C_6$–$C_{24}$aryloxy, a primary or secondary amine radical, $C_6$–$C_{12}$arylthio, $C_7$–$C_{25}$aralkyl, thienyl, benzo[b]thienyl, dibenzo[b,d]thienyl, thianthrenyl, furyl, furfuryl, 2H-pyranyl, benzofuranyl, isobenzofuranyl, benzimidazolyl, benzothiazolyl, dibenzofuranyl, phenoxythiinyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl O-thienyl, O-benzo[b]thienyl, O-dibenzo[b,d]thienyl, O-thianthrenyl, O-furyl, O-furfuryl, O-2H-pyranyl, O-benzofuranyl, O-isobenzofuranyl, O-benzimidazolyl, O-benzothiazolyl, O-dibenzofuranyl, O-phenoxythiinyl, O-pyrrolyl, O-imidazolyl, O-pyrazolyl, O-pyridyl, O-bipyridyl, O-triazinyl, O-pyrimidinyl, O-pyrazinyl, O-pyridazinyl, O-indolizinyl, O-isoindolyl, O-indolyl, O-indazolyl, O-purinyl, O-quinolizinyl, O-quinolyl, O-isoquinolyl, O-phthalazinyl, O-naphthyridinyl, O-quinoxalinyl, O-quinazolinyl, O-cinnolinyl, O-pteridinyl, O-carbazolyl, O-carbolinyl, O-benzotriazolyl, O-benzoxazolyl, O-phenanthridinyl, O-acridinyl, O-perimidinyl, O-phenanthrolinyl, O-phenazinyl, O-isothiazolyl, O-phenothiazinyl, O-isoxazolyl, O-furazanyl or O-phenoxazinyl S-thienyl, S-benzo[b]thienyl, S-dibenzo[b,d]thienyl, S-thianthrenyl, S-furyl, S-furfuryl, S-2H-pyranyl, S-benzofuranyl, S-isobenzofuranyl, S-benzimidazolyl, S-benzothiazolyl, S-dibenzofuranyl, S-phenoxythiinyl, S-pyrrolyl, S-imidazolyl, S-pyrazolyl, S-pyridyl, S-bipyridyl, S-triazinyl, S-pyrimidinyl, S-pyrazinyl, S-pyridazinyl, S-indolizinyl, S-isoindolyl, S-indolyl, S-indazolyl, S-purinyl, S-quinolizinyl, S-quinolyl, S-isoquinolyl, S-phthalazinyl, S-naphthyridinyl, S-quinoxalinyl, S-quinazolinyl, S-cinnolinyl, S-pteridinyl, S-carbazolyl, S-carbolinyl, S-benzotriazolyl, S-benzoxazolyl, S-phenanthridinyl, S-acridinyl, S-perimidinyl, S-phenanthrolinyl, S-phenazinyl, S-isothiazolyl, S-phenothiazinyl, S-isoxazolyl, S-furazanyl or S-phenoxazinyl, or $Q_3$ and $Q_4$ together are a lactam, quinomethylene, hydantoin, acenaphthenequinone, azlactone, pyrazolonyl, barbituric acid, isoindolinone or isoindoline radical, with the proviso that $Q_4$ is not hydrogen and $Q_3$ is not a primary or secondary amine radical if $R_3$ is hydrogen, methoxy or hydroxyl and $R_1$, $R_2$ and $R_4$ are hydrogen, and $X_2$ is thienyl, furyl, 2H-pyranyl, pyrrolyl, imidazolyl, pyrazolyl, pyridyl, triazinyl, pyrazinyl, pyridazinyl, morpholin, piperidyl, piperazinyl, or is

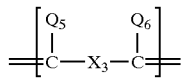

in which $X_3$ is a single bond, $C_6$–$C_{24}$arylene, thienylene, benzo[b]thienylene, dibenzo[b,d]thienylene, thianthrenylene, furylene, furfurylene, 2H-pyranylene, benzofuranylene, isobenzofuranylene, dibenzofuranylene, phenoxythinylene, pyrrolylene, imidazolylene, pyrazolylene, pyridylene, bipyridylene, benzimidazolylene, benzothiazolylene, triazinylene, pyrimidinylene, pyrazinylene, pyridazinylene, indolizinylene, isoindolylene, indolylene, indazolylene, purinylene, quinolizinylene, quinolylene, isoquinolylene, phthalazinylene, naphthyridinylene, quinoxalinylene, quinazolinylene, cinnolinylene, pteridinylene, carbazolylene, carbolinylene, benzotriazolylene, benzoxazolylene, phenanthridinylene, acridinylene, perimidinylene, phenanthrolinylene, phenazinylene, isothiazolylene, phenothiazinylene, isoxazolylene, furazanylene or phenoxazinylene 1,2-phenylene, 1,3-phenylene, 1,4-phenylene or naphthylene, or a tetravalent polyether, polyimine, polyamine radical, or bi($C_6$–$C_{24}$)arylene, bipyridylene, bipyrrolylen, piperazinedionylen, quinodimethylene, imidazolonylen, isoindolinylen, and anthraquinoylfuranoylen, $C_2$–$C_{24}$alkenylene, in which bi($C_6$–$C_{24}$)arylene, bipyridylene, bipyrrolylen, piperazinedionylen, quinodimethylene, imidazolonylen, isoindolinylen, and anthraquinoylfuranoylen or $C_2$–$C_{24}$alkenylene are optionally interrupted by one or more intermediate units selected from the group consisting of —CH=CH—, —CH=N—, —N=N—, —$CR_{44}R_{42}$—, —CO—, —COO—, —OCO—, —$NR_{42}$CO—, —$CONR_{42}$—, —O—, —S—, —SO—, —$SO_2$— or —$NR_{42}$—, in which $R_{42}$ and $R_{44}$ independently of one another are hydrogen, $C_1$–$C_{24}$alkyl, $C_5$–$C_{12}$cycloalkyl, $C_2$–$C_{24}$ alkenyl, $C_6$–$C_{24}$aryl, $C_7$–$C_{25}$aralkyl or thienyl, benzo[b]thienyl, dibenzo[b,d]thienyl, thianthrenyl, furyl, furfuryl, 2H-pyranyl, benzofuranyl, isobenzofuranyl, benzimidazolyl, benzothiazolyl, dibenzofuranyl, phenoxythiinyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, with the proviso that if $R_1$, $R_2$, $R_3$, $R_4$, $R_{100}$, $R_{200}$, $R_{300}$, $R_{400}$ are all tert-butyl or all hydrogen, $Q_5$ and $Q_6$ are hydrogen, $X_3$ is not 1,4-phenylene, and $Q_5$ and $Q_6$ independently of one another are hydrogen, $C_6$–$C_{24}$aryl, $C_6$–$C_{24}$aryloxy, $C_1$–$C_{24}$alkyl, $C_1$–$C_{24}$alkoxy, $C_1$–$C_{24}$alkylthio, $C_5$–$C_{12}$cycloalkyl, $C_5$–$C_{12}$cycloalkoxy, $C_5$–$C_{12}$cycloalkylthio, $C_2$–$C_{24}$alkenyl, $C_6$–$C_{24}$aryl, $C_6$–$C_{24}$aryloxy, $C_6$–$C_{24}$arylthio, thienyl, benzo[b]thienyl, dibenzo[b,d]thienyl, thianthrenyl, furyl, furfuryl, 2H-pyranyl, benzofuranyl, isobenzofuranyl, benzimidazolyl, benzothiazolyl, dibenzofuranyl, phenoxythiinyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, carbazoyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl O-thienyl, O-benzo[b]thienyl, O-dibenzo[b,d]thienyl, O-thianthrenyl, O-furyl, O-furfuryl, O-2H-pyranyl, O-benzofuranyl, O-isobenzofuranyl, O-benzimidazolyl, O-benzothiazolyl, O-dibenzofuranyl, O-phenoxythiinyl, O-pyrrolyl, O-imidazolyl, O-pyrazolyl, O-pyridyl, O-bipyridyl, O-triazinyl, O-pyrimidinyl, O-pyrazinyl, O-pyridazinyl, O-indolizinyl, O-isoindolyl, O-indolyl, O-indazolyl, O-purinyl, O-quinolizinyl, O-quinolyl, O-isoquinolyl, O-phthalazinyl, O-naphthyridinyl, O-quinoxalinyl, O-quinazolinyl, O-cinnolinyl, O-pteridinyl, O-carbazolyl, O-carbolinyl, O-benzotriazolyl, O-benzoxazolyl, O-phenanthridinyl, O-acridinyl, O-perimidinyl, O-phenanthrolinyl, O-phenazinyl, O-isothiazolyl, O-phenothiazinyl, O-isoxazolyl, O-furazanyl or O-phenoxazinyl S-thienyl, S-benzo[b]thienyl, S-dibenzo[b,d]thienyl, S-thianthrenyl, S-furyl, S-furfuryl, S-2H-pyranyl, S-benzofuranyl, S-isobenzofuranyl, S-benzimidazolyl, S-benzothiazolyl, S-dibenzofuranyl, S-phenoxythiinyl, S-pyrrolyl, S-imidazolyl, S-pyrazolyl, S-pyridyl, S-bipyridyl, S-triazinyl, S-pyrimidinyl, S-pyrazinyl, S-pyridazinyl, S-indolizinyl, S-isoindolyl, S-indolyl, S-indazolyl, S-purinyl, S-quinolizinyl, S-quinolyl, S-isoquinolyl, S-phthalazinyl, S-naphthyridinyl, S-quinoxalinyl, S-quinazolinyl, S-cinnolinyl, S-pteridinyl, S-carbazolyl, S-carbolinyl, S-benzotriazolyl, S-benzoxazolyl, S-phenanthridinyl, S-acridinyl, S-perimidinyl, S-phenanthrolinyl, S-phenazinyl, S-isothiazolyl, S-phenothiazinyl, S-isoxazolyl, S-furazanyl or S-phenoxazinyl, or $X_2$ is 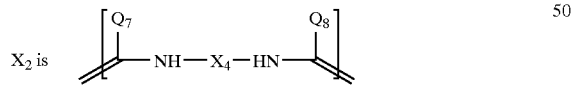

in which
$Q_7$ and $Q_8$ independently of one another are $Q_5$ or $Q_6$, and
$X_4$ is $C_6$–$C_{24}$arylene, $A_5$–$A_{18}$heteroarylene, a polymethylidene or divalent polyether, polyimine, polyamine radical, or bi($C_8$–$C_{24}$)arylene, bipyridylene, bipyrrolylen, piperazinedionylen, quinodimethylene, imidazolonylen, isoindolinylen, and anthraquinoylfuranoylen $C_2$–$C_{24}$alkenylene, in which bi($C_6$–$C_{24}$)arylene, bipyridylene, bipyrrolylen, piperazinedionylen, quinodimethylene, imidazolonylen, isoindolinylen, and anthraquinoylfuranoylen or $C_2$–$C_{24}$alkenylene are optionally interrupted by one or more intermediate units selected from the group consisting of —CH=CH—, —CH=N—, —N=N—, —CR$_{44}$R$_{42}$—, —CO—, —COO—, —OCO—, —NR$_{42}$CO—, —CONR$_{42}$—, —O—, —S—, —SO—, —SO$_2$— or —NR$_{42}$—, or $X_2$ is 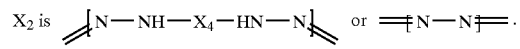

2. A compound according to claim 1 of the formula (XVI)

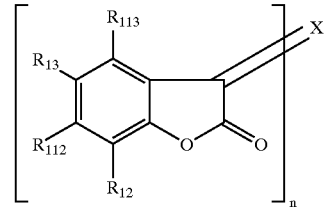

(XVI)

in which
n is 1 or 2, and
if n is 1
X is a hydrazone or imine radical, with the proviso that, if $R_{12}$, $R_{13}$, $R_{112}$ and $R_{113}$ are hydrogen, or at least one $R_{12}$, $R_{13}$, $R_{112}$ or $R_{113}$ is methyl, the hydrazone radical is excluded, or, if $R_{12}$, $R_{13}$, $R_{112}$ or $R_{113}$ is hydrogen, X is not phenylimine- or 4-dimethylamine-phenylimine,
or X is a methylene radical,

in which
$Q_3$ is a primary or secondary amine radical and $Q_4$ is hydrogen or $C_1$–$C_{24}$alkyl, —CO—($C_1$–$C_{24}$alkyl), —CO—O—($C_1$–$C_{24}$alkyl), $C_1$–$C_{24}$alkoxy, $C_1$–$C_{24}$alkylthio, $C_5$–$C_{12}$cycloalkyl, $C_5$–$C_{12}$cycloalkoxy, $C_5$–$C_{12}$cycloalkylthio, $C_2$–$C_{24}$alkenyl, $C_6$–$C_{24}$aryl, —CO—O—($C_6$–$C_{24}$aryl), —CO—($C_6$–$C_{24}$aryl), $C_6$–$C_{24}$aryloxy, a primary or secondary amine radical, $C_6$–$C_{12}$arylthio, $C_7$–$C_{25}$aralkyl, thienyl, benzothienyl, dibenzothienyl, thianthrenyl, furyl, furfuryl, 2H-pyranyl, benzofuranyl, isobenzofuranyl, benzimidazolyl, benzothiazolyl, dibenzofuranyl, phenoxythiinyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl O-thienyl, O-benzothienyl, O-dibenzothienyl, O-thianthrenyl, O-furyl, O-furfuryl, O-2H-pyranyl, O-benzofuranyl, O-isobenzofuranyl, O-benzimidazolyl, O-benzothiazolyl, O-dibenzofuranyl, O-phenoxythiinyl, O-pyrrolyl, O-imidazolyl, O-pyrazolyl, O-pyridyl, O-bipyridyl, O-triazinyl, O-pyrimidinyl, O-pyrazinyl, O-pyridazinyl, O-indolizinyl, O-isoindolyl, O-indolyl, O-indazolyl, O-purinyl, O-quinolizinyl, O-quinolyl, O-isoquinolyl, O-phthalazinyl, O-naphthyridinyl, O-quinoxalinyl, O-quinazolinyl, O-cinnolinyl, O-pteridinyl, O-carbazolyl, O-carbolinyl, O-benzotriazolyl, O-benzoxazolyl, O-phenanthridinyl, O-acridinyl, O-perimidinyl, O-phenanthrolinyl, O-phenazinyl, O-isothiazolyl, O-phenothiazinyl, O-isoxazolyl, O-furazanyl or O-phenoxazinyl S-thienyl, S-benzothienyl, S-dibenzothienyl, S-thianthrenyl, S-furyl, S-furfuryl, S-2H-pyranyl, S-benzofuranyl, S-isobenzofuranyl, S-benzimidazolyl, S-benzothiazolyl, S-dibenzofuranyl, S-phenoxythiinyl, S-pyrrolyl, S-imidazolyl, S-pyrazolyl, S-pyridyl, S-bipyridyl, S-triazinyl, S-pyrimidinyl, S-pyrazinyl, S-pyridazinyl, S-indolizinyl, S-isoindolyl, S-indolyl, S-indazolyl, S-purinyl, S-quinolizinyl, S-quinolyl, S-isoquinolyl, S-phthalazinyl, S-naphthyridinyl, S-quinoxalinyl, S-quinazolinyl, S-cinnolinyl, S-pteridinyl, S-carbazolyl, S-carbolinyl, S-benzotriazolyl, S-benzoxazolyl, S-phenanthridinyl, S-acridinyl, S-perimidinyl, S-phenanthrolinyl, S-phenazinyl, S-isothiazolyl, S-phenothiazinyl, S-isoxazolyl, S-furazanyl or S-phenoxazinyl, or $Q_3$ and $Q_4$ together are a lactam, quinomethylene, hydantoin, acenaphthenequinone, azlactone, pyrazolonyl, barbituric acid, isoindolinone or isoindoline radical, with the proviso that $Q_4$ is not hydrogen and $Q_3$ is not a primary or secondary amine radical if $R_{13}$ is hydrogen, methoxy or hydroxyl and $R_{12}$, $R_{112}$ and $R_{113}$ are hydrogen, and if n is 2

X is thienyl, furyl, 2H-pyranyl, pyrrolyl, imidazolyl, pyrazolyl, pyridyl, triazinyl, pyrazinyl, pyridazinyl, morpholin, piperidyl, piperazinyl, or is

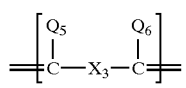

in which $X_3$ is a single bond, $C_6$–$C_{24}$arylene, thienylene, benzothienylene, dibenzothienylene, thianthrenylene, furylene, furfurylene, 2H-pyranylene, benzofuranylene, isobenzofuranylene, dibenzofuranylene, phenoxythinylene, pyrrolylene, imidazolylene, pyrazolylene, pyridylene, bipyridylene, benzimidazolylene, benzothiazolylene, triazinylene, pyrimidinylene, pyrazinylene, pyridazinylene, indolizinylene, isoindolylene, indolylene, indazolylene, purinylene, quinolizinylene, quinolylene, isoquinolylene, phthalazinylene, naphthyridinylene, quinoxalinylene, quinazolinylene, cinnolinylene, pteridinylene, carbazolylene, carbolinylene, benzotriazolylene, benzoxazolylene, phenanthridinylene, acridinylene, perimidinylene, phenanthrolinylene, phenazinylene, isothiazolylene, phenothiazinylene, isoxazolylene, furazanylene or phenoxazinylene 1,2-phenylene, 1,3-phenylene, 1,4-phenylene or naphthylene, or a tetravalent polyether, polyimine, polyamine radical, or bi($C_6$–$C_{24}$)arylene, bipyridylene, bipyrrolylene, piperazinedionylen, quinodimethylene, imidazolonylen, isoindolinylen, and anthraquinoylfuranoylen or $C_2$–$C_{24}$alkenylene, in which bi($C_6$–$C_{24}$)arylene, bipyridylene, bipyrrolylen, piperazinedionylen, quinodimethylene, imidazolonylen, isoindolinylen, and anthraquinoylfuranoylen or $C_2$–$C_{24}$alkenylene are optionally interrupted by one or more intermediate units selected from the group consisting of —CH═CH—, —CH═N—, —N═N—, —$CR_{44}R_{42}$—, —CO—, —COO—, —OCO—, —$NR_{42}$CO—, —CO$NR_{42}$—, —O—, —S—, —SO—, —SO$_2$— or —$NR_{42}$—, in which $R_{42}$ and $R_{44}$ independently of one another are hydrogen, $C_1$–$C_{24}$alkyl, $C_5$–$C_{12}$cycloalkyl, $C_2$–$C_{24}$alkenyl, $C_6$–$C_{24}$aryl, $C_7$–$C_{25}$aralkyl, thienyl, benzothienyl, dibenzothienyl, thianthrenyl, furyl, furfuryl, 2H-pyranyl, benzofuranyl, isobenzofuranyl, benzimidazolyl, benzothiazolyl, dibenzofuranyl, phenoxythiinyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, with the proviso that if $R_{12}$, $R_{13}$, $R_{112}$ or $R_{113}$ are all tert-butyl or all hydrogen, $Q_5$ and $Q_6$ are hydrogen, $X_3$ is not 1,4-phenylene, and $Q_5$ and $Q_6$ independently of one another are hydrogen, $C_6$–$C_{24}$aryl, $C_6$–$C_{24}$aryloxy, $C_1$–$C_{24}$alkyl, $C_1$–$C_{24}$alkoxy, $C_1$–$C_{24}$alkylthio, $C_5$–$C_{12}$cycloalkyl, $C_5$–$C_{12}$cycloalkoxy, $C_5$–$C_{12}$cycloalkylthio, $C_2$–$C_{24}$alkenyl, $C_6$–$C_{24}$aryl, $C_6$–$C_{24}$aryloxy, $C_6$–$C_{24}$arylthio, thienyl, benzothienyl, dibenzothienyl, thianthrenyl, furyl, furfuryl, 2H-pyranyl, benzofuranyl, isobenzofuranyl, benzimidazolyl, benzothiazolyl, dibenzofuranyl, phenoxythiinyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl O-thienyl, O-benzothienyl, O-dibenzothienyl, O-thianthrenyl, O-furyl, O-furfuryl, O-2H-pyranyl, O-benzofuranyl, O-isobenzofuranyl, O-benzimidazolyl, O-benzothiazolyl, O-dibenzofuranyl, O-phenoxythiinyl, O-pyrrolyl, O-imidazoyl, O-pyrazolyl, O-pyridyl, O-bipyridyl, O-triazinyl, O-pyrimidinyl, O-pyrazinyl, O-pyridazinyl, O-indolizinyl, O-isoindolyl, O-indolyl, O-indazolyl, O-purinyl, O-quinolizinyl, O-quinolyl, O-isoquinolyl, O-phthalazinyl, O-naphthyridinyl, O-quinoxalinyl, O-quinazolinyl, O-cinnolinyl, O-pteridinyl, O-carbazolyl, O-carbolinyl, O-benzotriazolyl, O-benzoxazolyl, O-phenanthridinyl, O-acridinyl, O-perimidinyl, O-phenanthrolinyl, O-phenazinyl, O-isothiazolyl, O-phenothiazinyl, O-isoxazolyl, O-furazanyl or O-phenoxazinyl S-thienyl, S-benzothienyl, S-dibenzothienyl, S-thianthrenyl, S-furyl, S-furfuryl, S-2H-pyranyl, S-benzofuranyl, S-isobenzofuranyl, S-benzimidazolyl, S-benzothiazolyl, S-dibenzofuranyl, S-phenoxythiinyl, S-pyrrolyl, S-imidazolyl, S-pyrazolyl, S-pyridyl, S-bipyridyl, S-triazinyl, S-pyrimidinyl, S-pyrazinyl, S-pyridazinyl, S-indolizinyl, S-isoindolyl, S-indolyl, S-indazolyl, S-purinyl, S-quinolizinyl, S-quinolyl, S-isoquinolyl, S-phthalazinyl, S-naphthyridinyl, S-quinoxalinyl, S-quinazolinyl, S-cinnolinyl, S-pteridinyl, S-carbazolyl, S-carbolinyl, S-benzotriazolyl, S-benzoxazolyl, S-phenanthridinyl, S-acridinyl, S-perimidinyl, S-phenanthrolinyl, S-phenazinyl, S-isothiazolyl, S-phenothiazinyl, S-isoxazolyl, S-furazanyl or S-phenoxazinyl, or

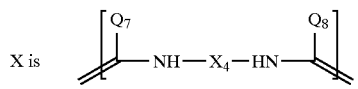

in which $Q_7$ and $Q_8$ independently of one another are $Q_5$ or $Q_6$, and $X_4$ is $C_6-C_{24}$arylene, $A_5-A_{18}$heteroarylene, a polymethylidene or divalent polyether, polyimine, polyamine radical, or bi($C_6-C_{24}$)arylene, bipyridylene, bipyrrolylen, piperazinedionylen, quinodimethylene, imidazolonylen, isoindolinylen, and anthraxquinoylfuranoylen $C_2-C_{24}$alkenylene, in which bi($C_6-C_{24}$)arylene, bipyridylene, bipyrrolylen, piperazinedionylen, quinodimethylene, imidazolonylen, isoindolinylen, and anthraquinoylfuranoylen or $C_2-C_{24}$alkenylene are optionally interrupted by one or more intermediate units selected from the group consisting of —CH=CH—, —CH=N—, —N=N—, —$CR_{44}R_{42}$—, —CO—, —COO—, —OCO—, —$NR_{42}CO$—, —$CONR_{42}$—, —O—, —S—, —SO—, —$SO_2$— or —$NR_{42}$—, or X is ⟍N—NH—$X_4$—HN—N⟋ or =N—N= .

and $R_{12}$, $R_{112}$, $R_{13}$ and $R_{113}$ independently of one another are hydrogen, halogen, OH, $NO_2$, $R_{14}$, $OR_{14}$, $OC_9-C_{18}$alkyl or $SC_9-C_{18}$alkyl, in which $R_{14}$ is $C_1-C_{24}$alkyl which is unsubstituted or substituted one or more times by oxo or by $COO^-X_5^+$ and which is uninterrupted or interrupted one or more times by O, N and/or S, or is $C_7-C_{18}$aralkyl or $C_6-C_{12}$aryl unsubstituted or substituted one or more times by halogen, $OR_{16}$, $NR_{16}R_{17}$, $COOR_{16}$, $CONR_{16}R_{17}$, $NR_{18}COR_{16}$ or $NR_{18}COOR_{16}$, $X_5^+$ is a cation $H^+$, $Na^+$, $K^+$, $Mg^{++}_{1/2}$, $Ca^{++}_{1/2}$, $Zn^{++}_{1/2}$, $Ar^{+++}_{1/3}$, or $(NR_{16}R_{17}R_{18}R_{19})^+$, and $R_{16}$ and $R_{17}$ independently of one another are hydrogen, $C_6-C_{12}$aryl, $C_7-C_{10}$aralkyl, or $C_1-C_8$alkyl which is unsubstituted or substituted one or more times by halogen, hydroxyl or $C_1-C_4$alkoxy, or $R_{16}$ and $R_{17}$ in $NR_{16}R_{17}$ or $CONR_{16}R_{17}$, together with the nitrogen atom connecting them, are pyrrolidine, piperidine, piperazine or morpholine each of which is unsubstituted or substituted from one to four times by $C_1-C_4$alkyl, and $R_{18}$ and $R_{19}$ independently of one another are hydrogen, $C_1-C_8$alkyl, $C_6-C_{10}$aryl or $C_6-C_{12}$aralkyl, or $R_{12}$ and $R_{112}$, $R_{112}$ and $R_{13}$, $R_{13}$ and $R_{113}$ independently of one another are each together divalent radicals.

* * * * *